United States Patent
Juan et al.

(10) Patent No.: US 6,512,104 B1
(45) Date of Patent: Jan. 28, 2003

(54) INTERLEUKIN-1β CONVERTING ENZYME LIKE CYSTEINE PROTEASE

(75) Inventors: Shao-Chieh Juan, Moorpark, CA (US); Frederick A. Fletcher, Camarillo, CA (US); Scott D. Patterson, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 08/724,378

(22) Filed: Oct. 1, 1996

(51) Int. Cl.⁷ .............................................. C07H 21/04
(52) U.S. Cl. ..................... 536/23.5; 435/69.1
(58) Field of Search ...................... 536/23.5; 435/320.1, 435/252.3, 69.1

(56) References Cited

U.S. PATENT DOCUMENTS

| | | |
|---|---|---|
| 4,179,337 A | 12/1979 | Davis et al. |
| 5,786,173 A | * 7/1998 | Alnemri et al. ............ 435/69.1 |

FOREIGN PATENT DOCUMENTS

| | | |
|---|---|---|
| WO | 96/00297 | 1/1996 |
| WO | 96/04387 | 2/1996 |
| WO | 97/35020 | 9/1997 |

OTHER PUBLICATIONS

Fernandes–Alnemri et al., J. Biol. Chem., vol. 269:30761–30764, Dec. 1994.*
Genbank sequence search, Jun. 18, 1997.*
Fernandes–Alnemri et al., Proc. Natl. Acad. Sci. 93, 7464–7469 (1996).
Abbas, Cell 84, 655–657 (1996).
Black et al. FEBS Lett. 247, 386–390 (1989).
Boldin et al. Cell 85, 803–815 (1996).
Cerretti et al., Science 256, 97–100 (1992).
Ellis and Horvitz, Cell 44, 817–829 (1986).
Ellis et al. Ann. Rev. Cell Biol. 7, 663–698 (1991).
Faucheu et al., EMBO J 14, 1914–1922 (1995).
Fernandes–Alnemri et al. Proc. Natl. Acad. Sci. USA 93, 7464–7469 (1996).
Fernandes–Alnemri et al., Cancer Res 55, 2737–2742 (1995).
Fernandes–Alnemri et al., Cancer Res 55, 6045–6052 (1995b).
Fernandes–Alnemri et al., J Biol Chem 269, 30761–30764 (1994).
Gagliardini et al. Science 263, 826–828, (1994.
Hengartner and Horvitz, Cell 76, 665–676 (1994b).
Hengartner and Horvitz, Curr. Opin. Genet. Dev. 4, 581–586 (1994a).
Hoffman and Liebermann, Oncogene 9, 1807–1812 (1994).
Hu et al., Journal of Biological Chemistry, 272 17255–17257 (1997).
Juan et al. Oncogene 13, 749–755 (1996).
Kamens et al., J Biol Chem 270, 15250–15256 (1995).
Kostura et al., Proc. Natl. Acad. Sci. USA 86, 5227–5231 (1989).
Kuida et al. Science 267, 2000–2003 (1995).
Kumar et al., Genes Dev 8, 1613–1626 (1994).
Lazebnik et al., Nature 371, 346–347 (1994).
Li et al. Cell 80, 401–411 (1995).
Lippke et al., J Biol Chem 271, 1825–1828 (1996).
Martin et al. EMBO J. 14, 5191–5200 (1995)).
Molineaux et al., Proc. Natl. Acad. Sci. USA 90, 1809–1813 (1993).
Munday et al., J Biol Chem 270, 15870–15876 (1995).
Muzio et al. Cell 85, 817–827 (1996).
Remington's Pharmaceutical Sciences, 18th ed. A.R. Gennaro, ed. Mack, Easton, PA (1980).
Sambrook et al. *Molecular Cloning: A Laboratory Manual* 2nd edition, Cold Spring Harbor Laboratory Press, Cold Spring Harbor, New York. (1989).
Thornberry et al., Nature 356, 768–774 (1992).
Vaux et al. Cell 76, 777–779 (1994).
Vincenz et al., Jpurnal of Biological Chemistry 272, 6578–6583 (1997).
Walker et al., Cell 78, 343–352 (1994).
Wang et al., Cell 78, 739–750 (1994).
White, Genes Dev. 10, 1–15 (1996).
Whyte, Trends Cell Biol. 6, 245–248 (1996).
Williams and Smith, Cell 74, 777–779 (1993).
Yuan and Horvitz, Development 116, 309–320 (1992.
Yuan et al. Cell, 75, 641–52 (1993).

* cited by examiner

*Primary Examiner*—Patrick Nolan
(74) *Attorney, Agent, or Firm*—Finnegan, Henderson, Farabow, Garrett & Dunner, L.L.P.

(57) ABSTRACT

A new member of a family of ICE-like cysteine proteases has been identified. The protease family is termed LICE (Like ICE) and the family member described herein is LICE3. LICE3 polypeptides, nucleic acids encoding LICE3 and vectors and host cells for the expression LICE3 are disclosed. Also disclosed are methods for identifying LICE3 agonists and antagonists, and methods for treatment of disorders characterized by altered apoptosis.

3 Claims, 8 Drawing Sheets

FIGURE 1A

```
  1  TTTTACCATGGTCTCATTTTAATACTGCTGGTGGAAAAGGAAATCGTGATGCAGCTTCCT

61  CAAAGTTGCTTCAAGAAAAGCTGAGCCATTACCTGGATATTGTGGAAGTAAACATTGCTC

121  ACCAGATCTCTCTACGTTCAGAAACATTGACTCAGAGAACTTAAAGGACATGATCTTCCT
                                                      M  I  F  L   4

181  TCTGAAAGACTCGCTTCCCAAAACTGAAATGACCTCCCTAAGTTTCCTGGCATTTCTAGA
      L  K  D  S  L  P  K  T  E  M  T  S  L  S  F  L  A  F  L  E  24

241  GAAACAAGGTAAAATAGATGAAGATAATCTGACATGCCTGGAGGACCTCTGCAAAACAGT
      K  Q  G  K  I  D  E  D  N  L  T  C  L  E  D  L  C  K  T  V  44

301  TGTACCTAAACTTTTGAGAAACATAGAGAAATACAAAAGAGAGAAAGCTATCCAGATAGT
      V  P  K  L  L  R  N  I  E  K  Y  K  R  E  K  A  I  Q  I  V  64

361  GACGCCTCCTGTAGACAAGGAAGCCGAGTCGTATCAAGGAGAGGAAGAACTAGTTTCCCA
      T  P  P  V  D  K  E  A  E  S  Y  Q  G  E  E  E  L  V  S  Q  84

421  AACAGATGTTAAGACATTCTTGGAAGCCTTACCGCAGGAGTCCTGGCAAAATAAGCATGC
      T  D  V  K  T  F  L  E  A  L  P  Q  E  S  W  Q  N  K  H  A 104

481  AGGTAGTAATGGTAACAGAGCCACAAATGGTGCACCAAGCCTGGTCTCCAGGGGGATGCA
      G  S  N  G  N  R  A  T  N  G  A  P  S  L  V  S  R  G  M  Q 124

541  AGGAGCATCTGCTAACACTCTAAACTCTGAAACCAGCACAAAGAGGGCAGCTGTGTACAG
      G  A  S  A  N  T  L  N  S  E  T  S  T  K  R  A  A  V  Y  R 144

601  GATGAATCGGAACCACAGAGGCCTCTGTGTCATTGTCAACAACCACAGCTTTACCTCCCT
      M  N  R  N  H  R  G  L  C  V  I  V  N  N  H  S  F  T  S  L 164

661  GAAGGACAGACAAGGAACCCATAAAGATGCTGAGATCCTGAGTCATGTGTTCCAGTGGCT
      K  D  R  Q  G  T  H  K  D  A  E  I  L  S  H  V  F  Q  W  L 184

721  TGGGTTCACAGTGCATATACACAATAATGTGACGAAAGTGGAAATGGAGATGGTCCTGCA
      G  F  T  V  H  I  H  N  N  V  T  K  V  E  M  E  M  V  L  Q 204

781  GAAGCAGAAGTGCAATCCAGCCCATGCCGACGGGGACTGCTTCGTGTTCTGTATTCTGAC
      K  Q  K  C  N  P  A  H  A  D  G  D  C  F  V  F  C  I  L  T 224
```

FIGURE 1B

```
841  CCATGGGAGATTTGGAGCTGTCTACTCTTCGGATGAGGCCCTCATTCCCATTCGGGAGAT
      H   G   R   F   G   A   V   Y   S   S   D   E   A   L   I   P   I   R   E   I   244

901  CATGTCTCACTTCACAGCCCTGCAGTGCCCTAGACTGGCTGAAAAACCTAAACTCTTTTT
      M   S   H   F   T   A   L   Q   C   P   R   L   A   E   K   P   K   L   F   F   264

961  CATCCAGGCCTGCCAAGGTGAAGAGATACAGCCTTCCGTATCCATCGAAGCAGATGCTCT
      I   Q   A   C   Q   G   E   E   I   Q   P   S   V   S   I   E   A   D   A   L   284

1021 GAACCCTGAGCAGGCACCCACTTCCCTGCAGGACAGTATTCCTGCCGAGGCTGACTTCCT
      N   P   E   Q   A   P   T   S   L   Q   D   S   I   P   A   E   A   D   F   L   304

1081 ACTTGGTCTGGCCACTGTTCCAGGCTATGCATCCTTTCGGCATGTGGAGGAAGGCAGCTG
      L   G   L   A   T   V   P   G   Y   A   S   F   R   H   V   E   E   G   S   W   324

1141 GTATATTCAGTCTCTGTGTAATCATCTGAAGAAATTGGTCCCAAGACATGAAGACATCTT
      Y   I   Q   S   L   C   N   H   L   K   K   L   V   P   R   H   E   D   I   L   344

1201 ATCCATCCTCACTGCTGTCAACGATGATGTGAGTCGAAGAGTGGACAAACAGGGAACAAA
      S   I   L   T   A   V   N   D   D   V   S   R   R   V   D   K   Q   G   T   K   364

1261 GAAACAGATGCCCCAGCCTGCTTTCACACTAAGGAAAAAACTAGTATTCCCTGTGCCCCT
      K   Q   M   P   Q   P   A   F   T   L   R   K   K   L   V   F   P   V   P   L   384

1321 GGATGCACTTTCATTATAGCAGAGAGTTTTTGTTGGTTCCTAGACCTCAAACGAATCATT
      D   A   L   S   L   *   389   (SEQ ID NO: 3)

1381 GGCTATAACCTCCAGCCTCCTGCCCAGCACAGGAATCGGTGGTCTCCACCTGTCATTCTA

1441 GAAACAGGAAACACCGTGTTTTCTGACACAGTCAATTCTGATTTTCTTTTTCTTTTGCAA

1501 GTCTAAATGTTAGAAAACTTTCTTTTTTTTGGAGATAGTCTCATTCTGTCACCCAGACTG

1561 GAGTGCAGGGGGGCAATCACGGCTCACTGTAGTCTCGGCCTCCCGGGCTCGGGCTGTCCT

1621 CCCGCCTCAGCTTCCCAAGTAGCTGGGACCACAGGTGTGTACCACCGTGCCCGGATTTTT

1681 TTTATTCCTTATTTTTTGTAGAGATGGAGGGATCTCACCTTGTTGCACAGGTGGGTTTCA
```

FIGURE 1C

```
1741  AACTCCTAGGCCCAAGTGATCCTCCCACCTCTGTCCCCAAAATACTGGGATTATAGGCAC

1801  GAGCCACCACACCTGGCCAGAAAACTTTCATTATTGAAGACTTGGATTGTAGCCTTGGTT

1861  TTGGATGTCTATTCTGAAGACAGAGTAATTGGCTTTGGTTTGTGCAGGTACTTTTTCTTT

1921  GAGACAGAGTCACTCCGTCACCTGGGCTGGAGTGCAGTGGTGGGATCACTGTTCACTGCA

1981  GCCTTGACCTCCCAGGTTCAAGCGATCCTCCCACCTCAGCCTCCCAAGTAGCTGAGACTA

2041  CAGGTGTGTGTCCATGCACAGCTAACTTTTTATTTTTTTGTGGAGATGGGGTTTCACTA

2101  TGTTGCCTAAGCTGGTCTCAAACTCCTGGGCTCAAGCGATCCTCCCACCTCA  2152
```

(SEQ ID NO: 1)

FIGURE 2A

```
Lice3   ..................................................
Lice2   ..................................................
Lice1   ..................................................
Mch2    ..................................................
Ice     ..................................................
Tx      ..................................................
Ich1    ..................................................
Ced-3   MMRQDRRSLLERNIMMFSSHLKVDEILEVLIAKQVLNSDNGDMINSCGTV   50

Lice3   .........................................MIFLLKDSL   9
Lice2   ..................................................
Lice1   ..................................................
Mch2    ..................................................
Ice     ..................................MADKVLKEKRKLFIRS  16
Tx      ..................................MAEGNHRKKPLKVLES  16
Ich1    .......MAADRGRRILGVCGMHPHHQETLKKNRVVLAKQLLLSELLEHL   43
Ced-3   REKRREIVKAVQRRGDVAFDAFYDALRSTGHEGLAEVLEPLARSVDSNAV  100

Lice3   PKTEMTSLSFLAFLEKQGKIDEDNLTCLEDLCKTVVPKLLRNIEKYKREK  59
Lice2   ..................................................
Lice1   ..................................................
Mch2    ..................................................
Ice     MGEGTINGLLDELLQTRVLNKEEMEKVKRENATVMDKTRALIDSVIPKGA  66
Tx      LGKDFLTGVLDNLVEQNVLNWKEEEKKKYYDAKTEDKVRVMADSMQEKQR  66
Ich1    LEKDIITLEMRELIQAKVGSFSQNVELLNLLPKRGPQAFDAFCEALRETK  93
Ced-3   EFECPMSPASHRRSRALSPAGYTSPTRVHRDSVSSVSSFTSYQDIYSRAR 150

Lice3   AIQIVTPPVDKEAESYQGEEELVSQTDVKTFLEALPQESWQNKHAGSNGN 109
Lice2   .......................MADDQGCIEEQGVEDSANEDSVDAKP  26
Lice1   ..................................MENTENSVDSKS    12
Mch2    ................................................MS  2
Ice     QACQICITYICEEDSYLAGTLGLSADQTSGNYLNMQDSQGVLSSFPAPQA 116
Tx      MAGQM...........LLQTF.FNIDQISPNK.............KAHPN  91
Ich1    QGHLEDMLLTT.....LSGLQHVLPPLSCDYDLSLPFPVCESCPLYKKLR 138
Ced-3   SRSRSRALHSSDRHNYSSPPVNAFPSQPSSANSSFTGCSSLGYSSSRNRS 200
```

FIGURE 2B

```
Lice3  RATNGAPSLVSRGMQGASA.NTLNSETSTKRAAV..YRM..NRNHRGLCV  154
Lice2  DRSSFVPSLFSKKKKNVTMRSIKTTRDRV.PTYQ..YNM..NFEKLGKCI   71
Lice1  IK.NLEPKIIHGSESMDSGISLDNS...........YKM..DYPEMGLCI   48
 Mch2  SASGLRRGHPAGGEENMTETDAFYKREMFDPAEK..YKM..DHRRRGIAL   48
  Ice  VQDNPAMPTSSGSEGNVKLCSLEEAQRIWKQKSAEIYPIMDKSSRTRLAL  166
   Tx  MEAGP..PESGESTDALKLCPHEEFLRLCKERAEEIYPIKERNNRTRLAL  139
 Ich1  LSTDTVEHSLDNKDGPVCLQVKPCTPEFYQTHFQLAYRL..QSRPRGLAL  186
Ced-3  FSKASGPTQYIFHEEDMNFVDAPTISRVFDEKTM..YRN..FSSPRGMCL  246
                          *

Lice3  IVNNHSFY...SLKDRQGTHKDAEILSHVFQWLGFTVHIHNNVTKVEMEM  201
Lice2  IINNKNFDKVTGMGVRNGTDKDAEALFKCFRSLGFDVIVYNDCSCAKMQD  121
Lice1  IINNKNFHKSTGMTSRSGTDVDAANLRETFRNLKYEVRNKNDLTREEIVE   98
 Mch2  IFNHERFFWHLTLPERRRTCADRDNLTRRFSDLGFEVKCFNDLKAEELLL   98
  Ice  IICNEEFD...SIPRRTGAEVDITGMTMLLQNLGYSVDVKKNLTASDMTT  213
   Tx  IICNTEFD...HLPPRNGADFDITGMKELLEGLDYSVDVEENLTARDMES  186
 Ich1  VLSNVHFTGEKELEFRSGGDVDHSTLVTLFKLLGYDVHVLCDQTAQEMQE  236
Ced-3  IINNEHFE...QMPTRNGTKADKDNLTNLFRCMGYTVICKDNLTGRGMLL  293
                       *

Lice3  VLQKQKCNPAHPTGDC.FVFCILTHGRFGAVYSSDEA.....LIPIREIM  245
Lice2  LLKKASE.EDHTNAAC.FACILLSHGEENVIYGKDGV......TPIKDLT  163
Lice1  LMRDVSK.EDHSKRSS.FVCVLLSHGEEGIIFGT.....NG.PVDLKKIT  140
 Mch2  KIHEVST.VSHADADC.FVCVFLSHGEGNHIYAYDAK......IEIQTLT  140
  Ice  ELEAFAHRPEHKTSDSTFL.VFMSHGIREGICGKKHSEQVPDILQLNAIF  262
   Tx  ALRAFATRPEHKSSDSTFL.VLMSHGILEGICGTVHDEKKPDVLLYDTIF  235
 Ich1  KLQNFAQLPAHRVTDSCI.VALLSHGVEGAIYGVDGK.....LLQLQEVF  280
Ced-3  TIRDFAKHESHGDSAIL...VILSHGEENVIIGVDDI.....PISTHEIY  335
                         *                  *

Lice3  SHFTALQCPRLAEKPKLFFIQACQGEEIQPSVSIEADALNPEQ......A  289
Lice2  AHFRGDRCKTLLEKPKLFFIQACRGTELDDG..IQADSG..........  200
Lice1  NFFRGDRCRSLTGKPKLFIIQACRGTELDCG..IETDSG..........  177
 Mch2  GLFKGDKCHSLVGKPKIFIIQACRGNQHDVPV.IPLDVVDNQTEKL..DT  187
  Ice  NMLNTKNCPSLKDKPKVIIIQACRGDSPGVV..WFKDSVGVSGNLSLPTT  310
   Tx  QIFNNRNCLSLKDKPKVIIVQACRGANRGEL..WVRDSPASLEVASSQSS  283
 Ich1  QLFDNANCPSLQNKPKMFFIQACRGDETDRG.VDQQDGKNHAGSPG....  325
Ced-3  DLLNAANAPRLANKPKIVFVQACRGERRDNG.FPVLDSVDGVP..AFLRR  382
```

FIGURE 2C

```
              *       .         .         .         .     *   .
Lice3  PTSLQDS...................IPAEADFLLGLATVPGYVSFRHV    319
Lice2  PINDTDA...............NPRYKIPVEADFLFAYSTVPGYYSWRSP    235
Lice1  ..VDDDMAC................HKIPVDADFLYAYSTAPGYYSWRNS    209
Mch2   NITEVDA...............ASVYTLPAGADFLMCYSVAEGYYSHRET    222
 Ice   EEFEDDAI...............KKAHIEKDFIAFCSSTPDNVSWRHP     343
  Tx   ENLEEDAV................YKTHVEKDFIAFCSSTPHNVSWRDS    316
 Ich1  .CEESDAGKEKL...........PKMRLPTRSDMICGYACLKGTAAMRNT    363
 Ced-3 GWDNRDGPLFNFLGCVRPQVQQ.VWRKKPSQADILIRYATTAQYVSWRNS    431

.         .         .         .
Lice3  EEGSWYI.QSLCNHLKKLVPRHEDILSILTAVNDDVSRRVDKQG......    362
Lice2  GRGSWFV.QALCSILEEH.GKDLEIMQILTRVNDRVARHFESQSDDPHFH    283
Lice1  KDGSWFI.QSLCAMLKQY.ADKLEFMHILTRVNRKVATEFESFSFDATFH    257
Mch2   VNGSWYI.QDLCEMLGKY.GSSLEFTELLTLVNRKVSQRRVDFCKDPSAI    270
 Ice   TMGSVFIGR.LIEHMQEY.....ACSCDVEEIFRKVRFSFEQPD......    381
  Tx   TMGSIFITQ.LITCFQKY.....SWCCHLEEVFRKVQQSFETPRA.....    355
 Ich1  KRGSWYIEA.LAQVFSE.RACDMHVADMLVKVNALIKDR.EGYAPGTEFH    410
 Ced-3 ARGSWFI.QAVCEVFSTH.AKDMDVVELLTEVNKKVACGFQTSQGSNIL.    478

.        .
Lice3  TKKQMPQP.AFTLRKKLVFPVPLDALSL    389     (SEQ ID NO: 3)
Lice2  EKKQIPCV.VSMLTKELYFSQ          303     (SEQ ID NO: 4)
Lice1  AKKQIPCI.VSMLTKELYFYH          277     (SEQ ID NO: 5)
Mch2   GKKQVPCF.ASMLTKKLHFFPKSN       293     (SEQ ID NO: 6)
 Ice   GRAQMPTTERVTLT..RCFYLFPGH      404     (SEQ ID NO: 7)
  Tx   .KAQMPTIER..LSMTRYFYLFPGN      377     (SEQ ID NO: 8)
 Ich1  RCKEMSEY.CSTLCRHLYLFPGHPPT     435     (SEQ ID NO: 9)
 Ced-3 ..KQMPEMTSRLLKK.FYFWPEARNSAV   503     (SEQ ID NO: 10)
```

INTERLEUKIN-1β CONVERTING ENZYME LIKE CYSTEINE PROTEASE

FIELD OF THE INVENTION

The invention relates to a novel cysteine protease having homology to interleukin-1β converting enzyme (ICE). The protease represents a member of a family of cysteine proteases termed LICE (Like ICE) which may be involved in modulating apoptosis.

BACKGROUND OF THE INVENTION

Programmed cell death, also called apoptosis, is essential for the maintenance of tissue size and cell number homeostasis of multi-cellular organisms, and also plays an important role in the development of diseases such as cancer, autoimmune disease, viral infection, and neurodegeneration. The importance of apoptosis in controlling cell proliferation as well as differentiation was not addressed until recently (for review, see Ellis et al. Ann. Rev. Cell Biol. 7, 663–698 (1991); Williams and Smith, Cell 74, 777–779 (1993); Vaux et al. Cell 76, 777–779 (1994); Hoffman and Liebermann, Oncogene 9, 1807–1812 (1994); White, Genes Dev. 10, 1–15 (1996); Abbas, Cell 84, 655–657 (1996). Molecular study of apoptosis was initiated in the nematode *Caenorhabditis elegans* whose development is strictly controlled by at least 14 genes regulating apoptosis (Ellis, supra; Hengartner and Horvitz, Curr. Opin. Genet. Dev. 4, 581–586 (1994a). Among these genes, ced-9 was found to suppress apoptosis and shared homology with the mammalian proto-oncogene Bcl-2 (Hengartner and Horvitz, Cell 76, 665–676 (1994b)). Other nematode genes, including ced-3 and ced-4, were required for programmed cell death to occur, and loss-of-function mutation in these two genes resulted in survival of cells that would normally undergo cell death (Ellis and Horvitz, Cell 44, 817–829 (1986); Yuan and Horvitz, Development 116, 309–320 (1992).

Structural analysis of the cloned ced-3 gene revealed the structural/functional homology between this gene product and a mammalian enzyme called interleukin-1β converting enzyme (ICE, Yuan et al. Cell, 75, 641–52 (1993). ICE cleaves the pro form of interleukin-1β (Black et al. FEBS Lett. 247, 386–390 (1989); Kostura et al., Proc. Natl. Acad. Sci. USA 86, 5227–5231 (1989)) and defined a new class of cysteine proteases (Cerretti et al., Science 256, 97–100 (1992); Thornberry et al., Nature 356, 768–774 (1992); Molineaux et al., Proc. Natl. Acad. Sci. USA 90, 1809–1813 (1993). However, it appeared that cleavage of IL-1β was not the only function of ICE. In cultured cells, over-expression of either CED-3 or ICE induced apoptosis (Miura et al., 1993). When ICE was introduced into dorsal root ganglia neurons by microinjection, it also triggered programmed cell death (Gagliardini et al. Science 263, 826–828, (1994). These data strongly suggested that both CED-3 and ICE contained a protease activity that was important for the control of programmed cell death, and that ICE or ICE-like cysteine protease(s) were involved in controlling mammalian apoptosis.

Although ICE shares strong homology with CED-3, its role in apoptosis is not well defined. Mice deficient in ICE develop normally and show little abnormality in tissue homeostasis (Li et al. Cell 80, 401–411 (1995); Kuida et al. Science 267, 2000–2003 (1995), suggesting that this subset of proteolytic enzymes might exhibit functional redundancy, or that ICE may not be involved in the major apoptotic mechanism.

A number of genes encoding putative cysteine proteases that share sequence homology with CED-3 and ICE have been described recently. ICE-related genes include Nedd2 or Ich1 (Kumar et al., Genes Dev 3, 1613–1626 (1994); Wang et al., Cell 78, 739–750 (1994), Tx, Ich2 or ICErelII (Faucheu et al., EMBO J 14, 1914–1922 (1995); Kamens et al., J Biol Chem 270, 15250–15256 (1995), ICErelIII (Munday et al., J Biol Chem 270, 15870–15876 (1995), Mch2 (Fernandes-Alnemri et al., Cancer Res 55, 2737–2742 (1995), CPP32β (Fernandes-Alnemri et al., J Biol Chem 269, 30761–30764 (1994); Tewari et al., Cell 81, 801–809 (1995), and Mch3 or CMH-1 (Fernandes-Alnemri et al., Cancer Res 5, 6045–6052 (1995b); Lippke et al., J Biol Chem 271, 1825–1828 (1996). ICErelIII has also been isolated as Ty (see PCT Application No. 96/04387). The mouse ortholog of CPP32β has also been reported (Juan et al. Oncogene 13, 749–755 (1996)).

The role of ICE-like proteases in controlling apoptosis suggests that they will be useful for regulating events surrounding programmed cell death. As apoptosis is likely to be important in disorders characterized by excessive cell death (e.g., autoimmune diseases, viral infections and nerve cell degeneration) and in disorders involving increased cell proliferation (e.g., cancer), it is an object of the invention to identify genes and their encoded polypeptides that are involved in apoptosis. It is a further object of the invention to identify additional ICE-related cysteine proteases for the purpose of identifying new genes and proteins that control apoptosis.

SUMMARY OF THE INVENTION

A novel member of a family of ICE-like cysteine proteases has been identified. The family of proteases is termed LICE (Like ICE) and the family member described herein is termed LICE3. Nucleic acid sequences encoding LICE3 and nucleic acid sequences which hybridize to LICE3 sequences as shown in FIG. 1 and remain hybridized under stringent conditions are encompassed by the invention. Vectors and host cells for the expression of LICE3-encoding nucleic acid sequences are also provided for.

LICE3 polypeptides and derivatives thereof which exhibit at least 60% homology with the LICE3 amino acid sequence as shown in FIG. 1 are also included. Methods of production of LICE3 polypeptides and antibodies or fragments thereof which specifically bind LICE3 are also considered part of the invention.

The observed homlogy between LICE3 and other ICE-related genes which are known to encode polypeptides that are involved in apoptosis, suggests that LICE3 is also involved in controlling apoptosis or programmed cell death. Therefore, compounds which block LICE3 activity may reduce the rate and/or extent of apoptosis. Methods for identifying compounds which interact with LICE3 and block its activity are encompassed by the invention. Methods for the treatment of disorders characterized by increased cell proliferation or increased apoptosis are also included.

DESCRIPTION OF THE FIGURES

FIGS. 1, 1A, 1B Nucleotide and predicted amino acid sequence of human LICE3 cDNA. The human cDNA contains a 389 amino acid open reading frame. Numbers on the left-hand side of the sequence indicate nucleotide positions, and numbers on the right-hand side indicate amino acid positions. Predicted translational start codon (ATG) as well as translational stop codons (TGA) are indicated by bold-faced type. The in-frame stop codon in the 5' untranslated region is underlined. The amino acid sequence QAC(R/Q)G, SEQ ID NOS. 15 or 16, critical for covalent linkage to the substrate is also underlined.

FIGS. 2, 2A, 2B, Sequence comparison of cysteine protease LICE3, SEQ ID NO: 3, LICE 2SEQ ID NO: 4, LICE 1, CPP32β SEQ ID NO: 5, Mch2SEQ ID NO: 6, ICE SEQ ID NO: 7, Tx SEQ ID NO: 8, Ich1SEQ ID NO: 9, and CED-3SEQ ID NO: 10. Amino acid sequences of human LICE 3 (LICE 3), human LICE 2 (LICE 2), human LICE 1/CPP32β(LICE1), human Mch2 (Mch2), human ICE, human Ich1, human Tx, and *C. elegans* CED-3 (CED3) were compiled to get the best alignment using the computer program MALIGNED. Residues conserved in 70% or more sequences (at least six of eight) are indicated in boldface. Potential aspartic acids cleavage sites (at positions 281 and 295) and the three residues required for substrate catalysis (Arg-167, His-225, and Arg-316) are shown in bold face and indicated with asterisks. The cysteine residue in QAC(R/Q) G, SEQ ID NOS. 15 or 16, required for catalytic binding is also indicated. Positions of the amino acid residues are as indicated.

DETAILED DESCRIPTION OF THE INVENTION

Figures 3A, 3B, 3C:
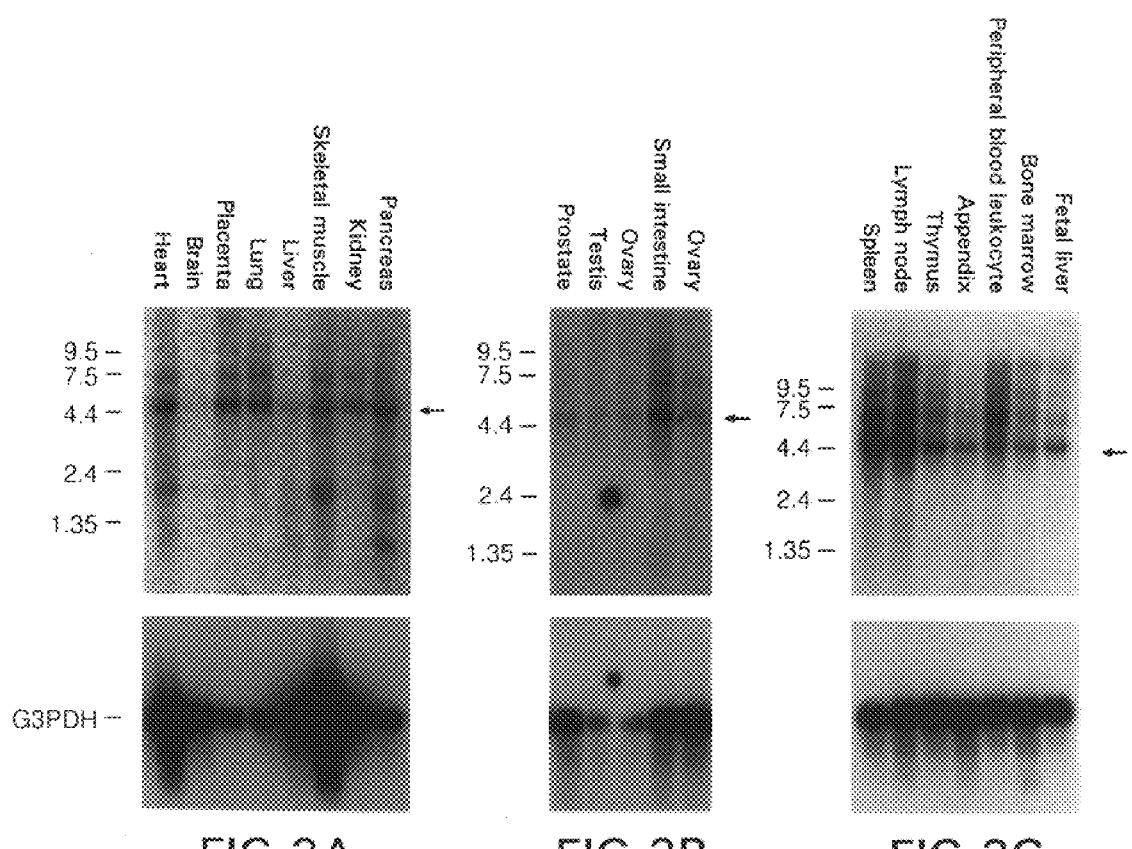
FIG. 3. Northern analysis of LICE 3 expression. Three human Northern blots of poly(A)$^+$ mRNA from various tissues, as indicated, were hybridized with a human LICE 3 random primed DNA probe. Numbers at the left-hand side indicate size. Expression level of glucose-3-phosphate dehydrogenase (G3PDH) gene is shown in the lower panel and was obtained by hybridizing the filter with a random-primed probe generated with a 1.1-kbp human G3PDH cDNA. Arrows at the right-hand side indicate the LICE 3 message.

A novel cysteine protease having homology to interleukin-1β converting enzyme (ICE) and other ICE-related polypeptides has been identified. An expressed sequence tag (EST) (GenBank accession no. T96912) having homology to ICE and CED-3 was amplified by polymerase chain reaction (PCR) and used to probe a human fetal liver cDNA library. The resulting full-length clone was sequenced and found to have significant homology to apoptosis genes ICE and CED-3 and to various other ICE-related genes encoding cysteine proteases. In particular, significant homology to CPP32β and Mch3α (CMH-1) was observed. CPP32β and Mch3α (CMH-1) are designated herein as members of a family of ICE-like proteases termed LICE (Like ICE). CPP32β is LICE1, Mch3α (CMH-1) is LICE2 and the new member described herein is LICE3.

The conserved sequence QACRG, SEQ ID NO: 15, present in ICE-related cysteine proteases which is implicated in substrate binding and catalysis is largely conserved in the presently isolated gene (the sequence QACQG, SEQ ID NO: 16, at residues 266–270 of LICE3 as shown in FIG. 2). Recent reports of two new ICE-like proteases, one designated alternatively as FLICE, MACH1, or Mch5 (Boldin et al. Cell 85, 803–815 (1996); Muzio et al. Cell 85, 817–827 (1996); Fernandes-Alnemri et al. Proc. Natl. Acad. Sci. USA 93, 7464–7469 (1996)) and a second designated Mch4 (Fernandes-Alnermi et al. ibid), also reveal a substrate binding site having the sequence QACQG, SEQ ID NO: 16. In addition, Mch4 has a predicted amino acid sequence which is identical with portions of the LICE3 amino acid sequence.

A Northern blot analysis using a 1.1 kb LICE3 DNA probe revealed LICE3 expression in a variety of tissues (see Example 2). Significantly, LICE3 expression was observed in spleen, lymph node and peripheral blood leukocyte suggesting a potential role for LICE3 in hematopoiesis. Expression of LICE3 in vitro in reticulocyte lysates (Example 3) and in *E. coli* (Example 4) is described. Extensive homology of LICE3 with ICE and CED-3 and conservation of amino acid residues in LICE3 required for cysteine protease activity indicates a role for LICE3 in apoptosis.

The invention provides for isolated nucleic acids encoding polypeptides having one or more of the biological activities of LICE3. As used herein, the term nucleic acid encompasses cDNA, genomic DNA, wholly or partially synthetic DNA or RNA. The biological activity of LICE3 polypeptides includes, but is not limited to, proteolytic activity and stimulation of apoptosis. Protease activity may be assayed by cleavage of an appropriate protein or peptide substrate. Substrates may include poly(ADP-ribose) polymerase (PARP) (Lazebnik et al., Nature 371, 346–347 (1994)), other proICE-like proteases; nuclear lamins A, B1/B2, and C; Gas2; protein kinase Cδ; sterol regulatory element binding proteins; and synthetic tetrapeptides such as DEVD, SEQ ID NO: 17, (Whyte, Trends Cell Biol. 6, 245–248 (1996)). LICE3 activity in stimulating apoptosis may be assayed by a variety of techniques including DNA fragmentation analysis (Martin et al. EMBO J. 14, 5191–5200 (1995)).

The nucleic acids of the invention are selected from the group consisting of:

a) the nucleic acid as shown in FIG. 1 (SEQ ID NO: 1) and its complementary strand;

b) nucleic acids which hybridize to the polypeptide coding regions of the nucleic acids shown in FIG. 1 (SEQ ID NO: 1) and remain hybridized to the nucleic acids under high stringency conditions; and c) nucleic acids which are degenerate to the nucleic acids of (a) or (b).

Generally, "high stringency" conditions refers to conditions of temperature and salt which are about 12–20° C. below the melting temperature ($T_m$) of a perfect hybrid of part or all of the complementary strands corresponding to SEQ. ID. NO: 1 or, alternatively, are about 12–20° C. below the $T_m$ of a perfect hybrid of part or all of the complementary strands corresponding to SEQ. ID. NO: 3. In one embodiment, "high stringency" conditions refer to conditions of about 65° C. and not more than about 1M Na$^+$. It is understood that salt concentration, temperature and/or length of incubation may be varied in either the first or second hybridization steps such that one obtains the hybridizing nucleic acid molecules according to the invention. Conditions for hybridization of nucleic acids and calculations of $T_m$ for nucleic acid hybrids are described in Sambrook et al. *Molecular Cloning: A Laboratory Manual* 2nd edition, Cold Spring Harbor Laboratory Press, Cold Spring Harbor, N.Y. (1989).

The nucleic acids of the invention may hybridize to part or all of the polypeptide coding region of LICE3 as shown in FIG. 1 (SEQ ID NO: 1) and therefore may encompass truncations or extensions of the nucleic acid in FIG. 1 (SEQ ID NO: 1). Truncated or extended nucleic acids are encompassed by the invention provided that they retain one or more of the biological properties of LICE3. The hybridizing nucleic acids may also include noncoding sequences located 5' and/or 3' to the LICE3 coding regions. Noncoding sequences include regulatory regions involved in LICE3 expression, such as promoters, enhancer regions, translational initiation sites, transcription termination sites and the like.

Nucleic acids of the invention encode biologically active LICE3 fragments and analogs. Examples of fragments include alterations in the nucleic acid sequence which result in truncated LICE3 molecules having a deletion of one or more amino acids at the carboxy terminus, the amino terminus, and/or at internal regions. In one embodiment, the nucleic acid will encode a polypeptide of at least about 10 amino acids. In another embodiment, the nucleic acid will encode a polypeptide of at least about 20 amino acids. In yet another embodiment, the nucleic acid will encode polypeptides of at least about 50 amino acids. Examples of analogs include alterations in the nucleic acid sequence which result in one or more amino acid substitutions or insertions in the LICE3 coding region.

Nucleic acid sequences encoding LICE3 fragments and analogs are generated using standard recombinant DNA methodology.

In a preferred embodiment, the nucleic acids of the invention encode human LICE3 as shown in FIG. 1 and SEQ ID NO: 1. A DNA clone having the sequence of human LICE3 coding region as shown in FIG. 1 has been deposited with the American Type Culture Collection, Rockville, Md. on Sep. 13, 1996 under accession no. 98168.

The nucleic acids of the invention will be linked with DNA sequences so as to express biologically active LICE3. Sequences required for expression are known to those skilled in the art and include promoters and enhancer sequences for initiation of RNA synthesis, transcription termination sites, ribosome binding sites for the initiation of protein synthesis, and leader sequences for secretion. Sequences directing expression and/or secretion of LICE3 may be homologous, i.e., they may be identical to or derived from those sequences in the genome involved in LICE3 expression and secretion, or may be heterologous, i.e., they may be present or derived from a different organism or host cell. A variety of plasmid vectors are available for expressing LICE3 in mammalian, plant, bacterial, insect, viral and yeast host cells. LICE3 coding regions may also be modified by substitution of preferred codons for optimal expression in a given host. Codon usage in bacterial, plant, insect, yeast and mammalian host systems is known and may be exploited by one skilled in the art to optimize mRNA translation. In addition, vectors are available for the tissue-specific expression of LICE3 in transgenic animals. Retroviral and adenovirus-based gene transfer vectors may also be used for the expression of LICE3 in human cells for in vivo therapy (see PCT Application No. 86/00922).

Nucleic acids of the invention may be used to identify the chromosomal locus of LICE3 and to identify aberrations in chromosomal LICE3 (e.g., translocations, deletions or insertions) which may be predictive of disease states. Part or all of the LICE3 sequence may be used a probe for chromosomal LICE3. Alterations in the LICE3 chromosomal gene may result in altered LICE3 expression that could increase or decrease the rate and/or extent of apoptosis in cells and affected tissues. It is anticipated that cells of the hematopoietic system (e.g. spleen and lymph node) may be most affected by altered LICE3 expression.

LICE3 nucleic acids may also be used to identify related genes which are ICE-like proteases. Nucleic acid probes can be made to conserved regions of ICE-like proteases and used to screen cDNA or genomic libraries by hybridization or polymerase chain reaction (PCR) for related molecules.

Nucleic acids of the invention may also be used as reagents for gene therapy and anti-sense therapy to modify the expression of LICE3 in selected tissues. LICE3 expression may be increased by modifying a targeted tissue with an expression vector containing the LICE3 coding region, wherein the vector produces LICE3 in a tissue specific manner. Gene therapy is used to treat a variety of conditions where increased apoptosis is desired, such as cancer. Endogenous LICE3 expression may be decreased by using anti-sense nucleic acids to a portion of the LICE3 coding region or to a control region operably linked thereto. The anti-sense nucleic acids may be the full-length LICE3 gene or to a fragment thereof which hybridizes to the endogenous LICE3 gene or a control region regulating expression of same. Anti-sense therapy is used to treat conditions where expression or overexpression of LICE3 is undesirable such as neurodegenerative diseases and viral infections where affected cells are undergoing apoptosis.

Nucleic acid sequences of the invention are also used to produce recombinant LICE3 as described below.

Procaryotic and eucaryotic host cells expressing LICE3 are also provided by the invention. Host cells include bacterial, yeast, plant, insect or mammalian cells. LICE3 may also be produced in transgenic animals such as mice or goats. Plasmids and vectors containing the nucleic acids of the invention are introduced into appropriate host cells using transfection or transformation techniques known to one skilled in the art. In a preferred embodiment, host cells contain DNA sequences encoding the LICE3 as shown in FIG. 1 and SEQ ID NO: 1. Examples of mammalian host cells for LICE3 expression include, but are not limited to COS, CHOd-, 293 and 3T3 cells.

ICE is expressed as a 404 amino acid polypeptide which is modified by cleavage at four aspartic acid residues. Two cleavage sites at Asp-257 and Asp-316 are indicated in FIG. 2. Mature ICE is a 30 kDa protein of two subunits of 10 kDa and 20 kDa. The remaining fragments generated by processing are not part of the mature polypeptide. The active form of ICE is believed to be a tetramer of two dimers each having a 10 kDa and 20 kDa subunit. (Thornberry et al., supra.) By analogy with ICE and other ICE-like proteases, LICE 3 is expressed as a proenzyme which is further processed by cleavage at aspartic acid residues to yield several proteolytic fragments. The term "proenzyme" when used in reference to LICE3 refers to a polypeptide resulting from the expression of LICE3-encoding DNA which is further processed by cleavage at one or more aspartic acid residues in the polypeptide. By comparision with cleavage sites of other ICE-like proteases, potential sites for LICE3 processing include aspartic acid residues at positions 281 and 295 (note alignment of sequences in FIG. 2). A third potential cleavage site may be located at the aspartic acid residue at position 86 although the alignment in this region with aspartic acid residues of other ICE-like proteases is less striking. Typically, two different molecular weight cleavage products of the proenzyme will associate into a multimeric form (usually a tetramer) to give the biologically active form. Potential fragments extending from residues 86–281 (about 21 kDa fragment) and residues 295–389 (about 10 kDa fragment) are likely to form active multimeric LICE3.

LICE3 polypeptides and fragments thereof which have at least one of the biological activities of LICE3 are encompassed by the invention. In one embodiment, full-length LICE3 polypeptides and fragments thereof have the amino acid sequence in FIG. 1 (SEQ ID NO: 2) or a portion thereof. The polypeptides may or may not have an amino terminal methionine residue. A LICE3 polypeptide may be a proenzyme expressed by the nucleic acid sequence as shown in FIG. 1 (SEQ ID NO: 1) or may comprise one or more proteolytic fragments thereof which are capable of associating to form a biologically active molecule. Potential polypeptide fragments span residues 86–281 and 295–389.

A derivative of LICE3 refers to a polypeptide having an addition, deletion, insertion or substitution of one or more amino acids such that the resulting polypeptide has at least one of the biological activities of LICE3. In a preferred embodiment, a LICE3 derivative will have at least about 60% homology to part or all of the amino acid sequence as shown in FIG. 1 (SEQ ID NO: 2) and have at least one of the biological activities of LICE3. The derivative may be naturally occurring, such as a polypeptide product of an allelic variant or a mRNA splice variant, or it may be constructed using techniques available to one skilled in the art for manipulating and synthesizing nucleic acids.

The invention also provides LICE3 as the product of procaryotic or eucaryotic expression of an exogenous DNA sequence, i.e., LICE3 is recombinant LICE3. Exogenous DNA sequences include cDNA, genomic DNA and synthetic DNA sequences. LICE3 may be the product of bacterial, yeast, plant, insect or mammalian cell expression. LICE3 produced in bacterial cells will have an N-terminal methionine residue. The invention also provides for a process of producing LICE3 comprising growing procaryotic or eucaryotic host cells transformed or transfected with nucleic acids encoding LICE3 and isolating polypeptide expression products of the nucleic acids.

Also included in the invention are LICE3 polypeptides which have undergone post-translational modifications (e.g., addition of N-linked or O-linked carbohydrate chains, processing of N-terminal or C-terminal ends), attachment of chemical moieties to the amino acid backbone, chemical modifications of N-linked or O-linked carbohydrate chains, and addition of an N-terminal methionine residue as a result of procaryotic host cell expression. The polypeptides may also be modified with a detectable label, such as an enzymatic, fluorescent, isotopic or affinity label to allow for detection and isolation of the protein.

LICE3 chimeric proteins comprising part or all of a LICE3 amino acid sequence fused to a heterologous amino acid sequence are also included. The heterologous sequence may be any sequence which allows the resulting fusion protein to retain the activity of LICE3. The heterologous sequences include, for example, immunoglobulin fusions, such as an Fc region of IgG, which provide dimerization, or fusions to enzymes which provide a label for the polypeptide, or fusions to secretory sequence which directs extracellular transport of LICE3.

The polypeptides of the invention are isolated and purified from tissues and cell lines which express LICE3 and from transformed host cells expressing LICE3. As LICE3 is normally produced as an intracellular protein, it will be isolated from cell lysates. Isolated LICE3 polypeptide is substantially free from association with human proteins and other cell constituents.

A method for the purification of LICE3 from natural sources (e.g. tissues and cell lines which normally express LICE3) and from transfected host cells is also encompassed by the invention. The purification process may employ one or more standard protein purification steps in an appropriate order to obtain purified protein. The chromatography steps can include ion exchange, gel filtration, hydrophobic interaction, reverse phase, chromatofocusing, affinity chromatography employing an anti-LICE3 antibody or biotin-streptavidin affinity complex and the like.

Also provided by the invention are chemically modified derivatives of LICE3 which provide additional advantages such as increased stability, longer circulating time, or decreased immunogenicity (see for example U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

LICE3 polypeptides are useful for the identification of agonists and antagonists. In general, LICE3 will be a target to screen candidate substances for the ability to alter LICE3 biological activity. Identification of potential agonists or antagonists may be readily accomplished by assaying LICE3-mediated cleavage of a variety of protein substrates in the presence of candidate substances. Protein substrates suitable for assaying LICE3 activity have been described above.

LICE3 polypeptides are useful for generating antibodies which specifically bind LICE3. Anti-LICE3 antibodies are prepared using methods and reagents available to one skilled in the art. The antibodies are useful in diagnostic applications or may have therapeutic value as agonist or antagonists.

LICE3 polypeptides are intracellular regulators of apoptosis. Modulation of LICE3 levels in cells may be useful in the treatment of disorders characterized by increased apoptosis (excessive cell death) or by decreased apoptosis (excessive cell proliferation). To be used directly as a therapeutic, a LICE3 polypeptide should be in a form that is taken up by target cells. Alternatively, LICE3 agonists or antagonists may be used to modulate intracellular LICE3 levels and thereby treat apoptosis disorders.

Methods for indentifying compounds which interact with LICE3 are also encompassed by the invention. The method comprises incubating LICE3 with a compound under conditions which permit binding of the compound to LICE3 and measuring the extent of binding. The compound may be substantially purified or present in a crude mixture. Binding compounds may be proteins, peptides, carbohydrates or small molecular weight organic compounds. The compounds may be further characterized by their ability to enhance or reduce LICE3 biological activity and therefore act as LICE3 agonists or as LICE3 antagonists.

The invention also encompasses LICE3 antagonists/inhibitors and the methods for obtaining them. An antagonist will reduce or eliminate one or more of the biological activities of LICE3 As an example, a LICE3 antagonist may reduce the rate and/or extent of apoptosis. LICE3 antagonists include substances which bind to LICE3 or to LICE3 effectors or activators in a manner that blocks LICE3 activity or the generation of active LICE3 molecules. LICE3 activity may be blocked by substances which bind to LICE3 at the catalytic site QACQG SEQ ID NO: 16 or by substances which bind to LICE3 and induce a conformational change such that the catalytic site is no longer accessible to substrate molecules. Examples of LICE3 antagonists are polypeptides or peptides (e.g. anti-LICE3 antibodies or fragments thereof), carbohydrates, and small molecular weight organic molecules. In one embodiment, antagonists include peptide derivatives of cleavage sequences (such as the tetrapeptide DEVD) SEQ ID NO: 17 which have been chemically modified such that binding to LICE3, but not substrate cleavage, occurs. Peptide substrats may be converted to antagonists by modification to aldehyde and fluoro/chloromethylketone derivatives. LICE3 antagonists of this type may be readily assayed by the ability to block LICE3-mediated cleavage of a protein or peptide substrate such as those described above. Other antagonists include substances which regulate LICE3 expression and typically include nucleic acids which are complementary to nucleic acids encoding LICE3 and which act as anti-sense regulators of expression.

LICE3 agonists may also be obtained which stimulate at least one of the biological activities of LICE3. Agonists may increase the rate and/or extent of LICE3 activity. Agonists include polypeptides and peptides, carbohydrates and small molecular weight organic molecules.

Antibodies specifically binding the LICE3 polypeptides of the invention are also encompassed by the invention. The antibodies may be produced by immunization with full-length LICE3 (proenzyme form), or one or more peptide fragments thereof, and the antibodies may be polyclonal or monoclonal. In addition, the antibodies of the invention may be recombinant, such as chimeric antibodies wherein the murine constant regions on light and heavy chains are replaced by human sequences, or CDR-grafted antibodies wherein only the complementary determining regions are of murine origin. Antibodies of the invention may also be human antibodies prepared, for example, by immunization of transgenic animals capable of producing human antibodies (see, for example, PCT Application No. WO93/12227). The antibodies are useful for detecting LICE3 in biological samples, thereby allowing the identification of cells or tissues which produce LICE3 and providing a quantitative measure of LICE3 expression. In addition, antibodies or fragments thereof which bind to LICE3 may be used to block the effects of LICE3.

The invention also provides for pharmaceutical compositions comprising a therapeutically effective amount of a LICE3 polypeptide, a LICE3 agonist or a LICE3 antagonist together with a pharmaceutically acceptable diluent, carrier, solubilizer, emulsifier, preservative and/or adjuvant. The term "therapeutically effective amount" means an amount which provides a therapeutic effect for a specified condition and route of administration. The composition may be in a liquid or lyophilized form and comprises a diluent (Tris, acetate or phosphate buffers) having various pH values and ionic strengths, solubilizers such as Tween or Polysorbate, carriers such as human serum albumin or gelatin, preservatives such as thimerosal or benzyl alcohol, and antioxidants such as ascorbic acid or sodium metabisulfite. Also encompassed are compositions comprising a LICE3 polypeptide, agonist and antagonist modified with a water soluble polymer to increase solubility, stability, plasma half-life and bioavailability. Compositions may also comprise incorporation of a LICE3 polypeptide, agonist or antagonist into liposomes, microemulsions, micelles or vesicles for controlled delivery over an extended period of time. Selection of a particular composition will depend upon a number of factors, including the condition being treated, the route of administration and the pharmacokinetic parameters desired. A more extensive survey of component suitable for pharmaceutical compositions is found in *Remington's Pharmaceutical Sciences*, 18th ed. A. R. Gennaro, ed. Mack, Easton, Pa. (1980).

Compositions of the invention may be administered by injection, either subcutaneous, intravenous or intramuscular, or by oral, nasal, pulmonary or rectal administration. The route of administration eventually chosen will depend upon a number of factors and may be ascertained by one skilled in the art.

The invention also provides for pharmaceutical compositions comprising a therapeutically effective amount of the nucleic acids of the invention together with a pharmaceutically acceptable adjuvant. Nucleic acid compositions will be suitable for the delivery of part or all of the LICE3 coding region and/or flanking regions to cells and tissues as part of an anti-sense therapy regimen.

Methods for the treatment of disorders characterized by either increased apoptosis or, alternatively, increased cell proliferation are also encompassed by the invention. Administration of a therapeutically effective amount of a LICE3 polypeptide or a LICE3 agonist may be used to treat cancers by promoting apoptosis of tumor cells. Alternatively, administration of a therapeutically effective amount of a LICE3 antagonist may be used to treat conditions resulting from increased apoptosis, such as viral infections (e.g., AIDS), nervous system degeneration (e.g., Parkinson's disease, Alzheimer's disease) and autoimmune diseases. A LICE3 agonist may stimulate the activity of LICE3 or increase levels of LICE3 expression; a LICE3 antagonist may block activity of LICE3 or decrease levels of LICE3 expression. Treatments may be employed using LICE3 polypeptides or LICE3 agonists alone or in combination with other agents which increase apoptosis when it is desired to treat disorders characterized by increased cell proliferation. LICE3 antagonists may be used alone or in combination with other agents which block apoptosis when it is desired to treat disorders characterized by increased apoptosis.

The following examples are offered to more fully illustrate the invention, but are not be construed as limiting the scope thereof.

EXAMPLE 1

Cloning and Sequencing of LICE3

Polymerase chain reaction (PCR) was carried out with human spleen QUICK-Clone cDNA (Clontech, Palo Alto, Calif.) as template using the following DNA oligonucleotides as primers:

(1082-24)

5'-CCATCGAAGCAGATGAACCCTGAG-3' (SEQ ID NO: 11)

(1082-26)

5-AGGTTGGCTGAAGATCTGTTTAAGCACCCC-3' (SEQ ID NO: 12)

The resulting PCR generated DNA fragment corresponded to the sequence of GenBank expressed sequenced tag (EST) clone #T96912, entered Mar. 27, 1995. This DNA fragment was subcloned into pCRII vector (Invitrogen) and was used to generate antisense riboprobe for screening. A $^{32}$P-labelled riboprobe was used to screen 780,000 plaques of human fetal liver library (Cat#HL1064a, Clontech). Hybridization was performed in Stark's solution (50% formamide, 50 mM potassium phosphate, 5×SSC, 1% SDS, 5×Denhardt's, 0.05% Sarcosyl, and 300 mg/mL salmon sperm DNA) at 42° C. Filters were then washed to a final stringency of 0.1×SSC, 55° C. After two rounds of screening, two positive clones, 5-1 and 13-1, were obtained. Inserts from these two clones were amplified by PCR using the following primers flanking the cloning sites of the λ vector:

5'-CCTTTTGAGCAAGTTCAGCCTGGTTAAGTCC-3' (1065-30) for the left arm (SEQ ID NO: 13)

5'-CAGAGGTGGCTTATGAGTATTTCTTCCAGGG-3' (1065-31) for the right arm (SEQ ID NO: 14)

PCR products were then subcloned into pCRII vector for sequencing. DNA sequencing was performed on both template strands using Taq DyeDeoxy Terminator Cycle Sequencing (Applied Biosystems, Inc., Foster City, Calif.)

on an automated DNA sequencer (Model 373A, Applied Biosystems). A long open reading frame of 389 amino acids was identified. The cDNA sequence is shown in FIG. 1.

A comparison of the sequence shown in FIG. 1 with ICE and CED-3 and other ICE-related protease genes revealed a strong similarity (see FIG. 2). Significantly, LICE3 had a sequence QACQG, SEQ ID No. 16, at residues 266 to 270 which is similar to the sequence QACRG, SEQ ID No. 15, which is present in CED-3 and all other ICE-related protease genes shown in FIG. 2. This sequence defines the site for covalent substrate binding and catalysis. This site is located between amino acid residue 162 and 166 of human CPP32β/Lice1 and between amino acid residue 283 and 287 of human ICE. CED-3-like cysteine proteases are cleaved at two conserved aspartic acid residues, Asp-297 and Asp-316 for ICE, and Asp-175 and Asp-181 for CPP32β/Lice1, to form mature enzyme (Thornberry et al., supra; Fernandes-Alnemri et al., supra; Juan et al., supra). Both aspartic acid residues were present in human Lice3 (FIG. 2). In addition, two other aspartic acid residues in the 5' region of ICE are cleavage sites, and it is likely that LICE 3 may also have additional cleavage sites. The residues required for substrate recognition, Arg-178, His-237, and Arg-341 of human ICE (Walker et al., Cell 78, 343–352 (1994); Wilson et al., 1994; Fernandes-Alnemri et al., supra; Juan et al., supra, were also conserved in human Lice3 (FIG. 2). Overall, LICE3 shows homology to other ICE-related cysteine proteases ranging from about 43 to 57% (see Table 1). LICE3 is most closely related to LICE2 having about 57% homology with LICE2.

The LICE3 mRNA is approximately 4 kb, and is expressed in a variety of human tissues, including heart, placenta, lung, liver, skeletal muscle, kidney, pancreas, prostate, small intestine, ovary, spleen, lymph node, thymus, appendix, and peripheral blood leukocyte, bone marrow, and fetal liver (see FIG. 3). Lice3 is highly expressed in hematopoietic tissues such as spleen and lymph node, suggesting that it may play a role in hematopoiesis. Human brain is the only tissue in which LICE3 mRNA expression is not observed. The expression pattern of LICE3 is distinguishable from that of CPP32β/LICE1, whose expression is detectable in brain.

EXAMPLE 3

Expression of LICE3 in Reticulocyte Lysates

The full-length LICE3 sequence, cloned into an in vitro translation vector (pCITE-4b containing an S-tag N-terminal fusion sequence, Novagen), was used to express the protein using the Promega's TnT T7-Coupled Reticulocyte Lysate System with precharged *E. coli* lysine tRNA biotinylated at the ε-amino acid group to label the protein. Reactions were set up according to the manufacturer's recommendations and incubated at 30° C. for 90 min. An aliquot of each reaction, together with molecular mass markers, was resolved on a pre-cast 10% NuPAGE gel (Novex) and transferred to nitrocellulose membrane (0.45 μm, Schleicher and Schuell) according to the manufacturer's instructions. The membrane was dried, blocked, and incubated with

TABLE 1

Similarity

|  | ICE | TX | ICEre13 | ICH-1 | LICE3 | MCH-2 | CED-3 | LICE1 | LICE2 |
|---|---|---|---|---|---|---|---|---|---|
| LICE2 | 50.82 | 51.24 | 51.65 | 51.56 | 56.86 | 57.72 | 59.84 | 69.26 |  |
| LICE1 | 52.85 | 53.23 | 49.81 | 52.90 | 55.10 | 56.32 | 57.62 |  | 54.86 |
| CED-3 | 54.48 | 51.49 | 51.35 | 52.43 | 50.52 | 55.44 |  | 34.57 | 36.95 |
| MCH2 | 52.03 | 50.92 | 50.74 | 51.75 | 55.60 |  | 34.74 | 38.27 | 39.43 |
| LICE3 | 44.80 | 43.10 | 44.50 | 47.23 |  | 34.74 | 28.00 | 32.45 | 38.71 |
| ICH-1 | 52.90 | 51.62 | 51.83 |  | 28.00 | 28.67 | 28.40 | 28.99 | 31.25 |
| ICEre13 | 64.36 | 83.25 |  | 27.23 | 23.59 | 27.21 | 24.94 | 29.66 | 28.10 |
| TX | 68.17 |  | 73.94 | 27.30 | 22.53 | 27.84 | 26.29 | 31.94 | 26.86 |
| ICE |  | 52.79 | 50.27 | 27.63 | 23.73 | 29.15 | 28.65 | 30.42 | 26.23 |

Identity

EXAMPLE 2

Northern Blot Analysis of LICE3 Expression

A 1.1 kb DNA fragment, obtained by digesting the pCRII vector containing LICE3 cDNA with EcoRI, was used as a template to generate DNA probe using random primed DNA labeling kit (Boehringer Mannheim). Three human multiple tissue Northern blots (Cat#7759-1, 7760-1, and 7754-1, Clontech) were hybridized with this DNA probe in Stark's solution overnight at 42° C. The filters were washed briefly with 6×SSC at room temperature, then twice with 2×SSC and 0.1% SDS at 42° C. for 15 min, twice with 1×SSC and 0.1% SDS at 42° C. for 15 min, and twice with 0.5×SSC and 0.1% SDS at 42° C. for 15 min. The filters were then exposed to Kodak X-ray film for 2 days prior to development. For an internal control, the filters were hybridized with a random-primed cDNA probe of a 1.1-kb human glyceraldehyde 3-phosphate dehydrogenase (G3PDH, Clontech) under the same conditions.

Figure 4:
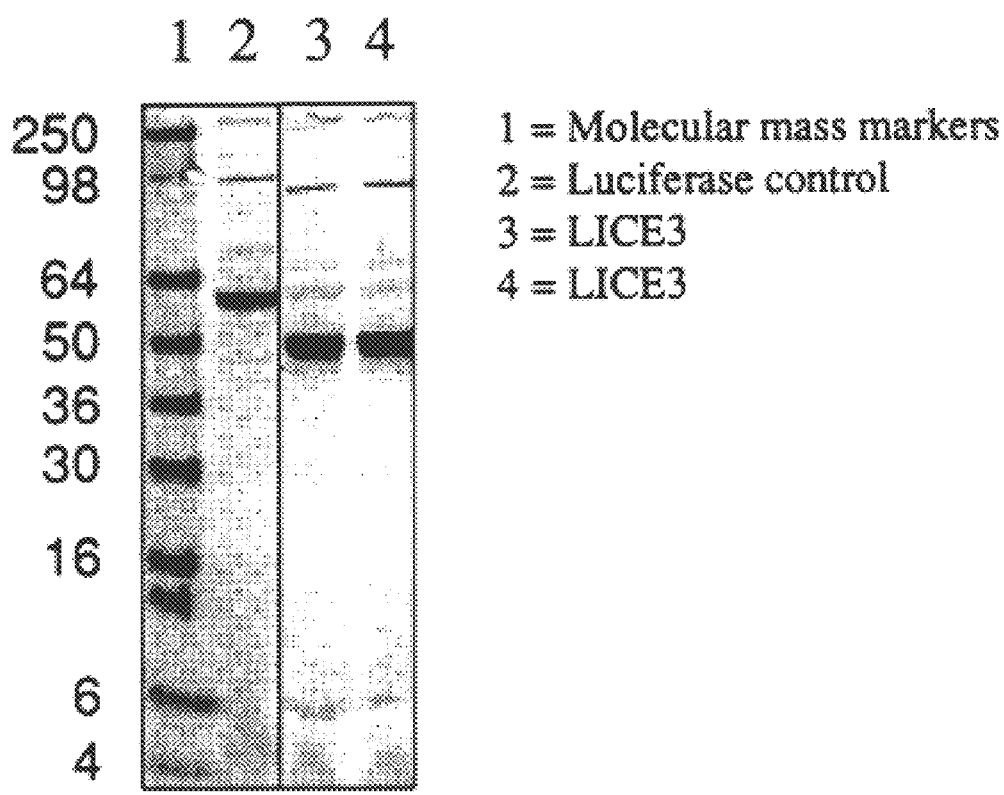
FIG. 4. Expression of LICE3 polypeptide in reticulocyte lysates. Expression was carried out as described in Example 3.

Streptavidin-Alkaline phosphatase (which recognizes biotinylated proteins). After washing, the relevant proteins were detected using Western Blue Stabilized Substrate for Alkaline phosphatase (Promega). FIG. 4 shows an image of the membrane. The relative molecular mass of the markers, in kDa, is shown to the left of the image. The Luciferase control and LICE3 proteins migrate at their expected relative molecular mass.

EXAMPLE 4

Expression of LICE3 in *E. coli* lysates

The full-length LICE3 sequence was cloned into an *E. coli* expression vector in which an oligohistidine sequence was introduced at the N-terminus of the protein. The resulting plasmid was transformed into BL21(DE3)LysS strain of *E. coli* (Novagen, Madison, Wis.) using standard techniques. Transformants were grown overnight at 37° C. in LBamp and the overnight cultures were diluted 1:100 in fresh LBamp. Cultures were grown at 30° C. until an $OD_{600}$ of 0.8–1.0 was attained and then 0.5 mM isopropyl-β-D-thiogalactosidase was added and the cultures incubated at 30° C. for 3 hr to induce expression of the fusion protein. Cells were pelleted and washed with phosphate buffered saline (PBS) before being resuspended in lysis buffer (50 mM HEPES, pH 7.4, 150 mM NaCl, 2 mM EDTA, 1% NP-40) containing 1% Aprotinin, 1 μg/ml Leupeptin, 1 μg/ml Pepstatin, 1 μg/ml E64, and 1 mM PMSF. Cells were lysed by sonication for 2 min in a water bath sonicator (Branson Ultrasonics Corp., Danbury, Conn.) and the subsequent lysates centrifuged at 5,000×g for 10 min. Aliquots from the insoluble pellet and the soluble fraction, together with molecular mass markers, were resolved on a pre-cast 10% NUPAGE gel (Novex, San Diego, Calif.) and transferred to nitrocellulose membrane (0.45 μm, Schleicher and Schuell, Keene, N.H.) according to the manufacturer's instructions. Probing of the membrane with antibodies directed against the polyhistidine domain of the vector (Santa Cruz Biotechnology, Santa Cruz, Calif.) detected a protein only in the insoluble pellet of cells. The protein migrated at $M_r$ ~49,000, close to the expected relative molecular mass ($M_r$ ~46,000) of the full length HIS-LICE3 fusion protein. It is possible that some of the fusion protein was expressed in the soluble fraction of cells but the oligohistidine sequence had been removed by autoprocessing by the protease. Recombinant LICE3 protein from the insoluble fraction of cells is purified and refolded.

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. An isolated nucleic acid encoding a polypeptide, wherein the nucleic acid comprises the polypeptide-coding region of FIG. 1 (SEQ ID NO: 1) or a sequence that is degenerate to the polypeptide-coding region.

2. A nucleic acid encoding a polypeptide comprising the amino acid sequence of SEQ ID NO: 3.

3. An expression vector comprising a nucleic acid, wherein the nucleic acid comprises the polypeptide-encoding region as shown in FIG. 1 (SEQ ID NO: 1) or a sequence that is degenerate to the polypeptide-encoding region.

* * * * *

SEQUENCE LISTING

<160> NUMBER OF SEQ ID NOS: 17

<210> SEQ ID NO 1
<211> LENGTH: 2152
<212> TYPE: DNA
<213> ORGANISM: Homo sapiens
<220> FEATURE:
<221> NAME/KEY: CDS
<222> LOCATION: (170)..(1336)

<400> SEQUENCE: 1

```
ttttaccatg gtctcatttt aatactgctg gtggaaaagg aaatcgtgat gcagcttcct      60
caaagttgct tcaagaaaag ctgagccatt acctggatat tgtggaagta acattgctc     120 accagatctc tctacgttca gaaacattga ctcagagaac ttaaaggac atg atc ttc    178
                                                      Met Ile Phe
                                                        1 ctt ctg aaa gac tcg ctt ccc aaa act gaa atg acc tcc cta agt ttc      226
Leu Leu Lys Asp Ser Leu Pro Lys Thr Glu Met Thr Ser Leu Ser Phe
      5                  10                  15 ctg gca ttt cta gag aaa caa ggt aaa ata gat gaa gat aat ctg aca      274
Leu Ala Phe Leu Glu Lys Gln Gly Lys Ile Asp Glu Asp Asn Leu Thr
 20                  25                  30                  35 tgc ctg gag gac ctc tgc aaa aca gtt gta cct aaa ctt ttg aga aac      322
Cys Leu Glu Asp Leu Cys Lys Thr Val Val Pro Lys Leu Leu Arg Asn
                 40                  45                  50 ata gag aaa tac aaa aga gag aaa gct atc cag ata gtg acg cct cct      370
Ile Glu Lys Tyr Lys Arg Glu Lys Ala Ile Gln Ile Val Thr Pro Pro
             55                  60                  65 gta gac aag gaa gcc gag tcg tat caa gga gag gaa gaa cta gtt tcc      418
Val Asp Lys Glu Ala Glu Ser Tyr Gln Gly Glu Glu Glu Leu Val Ser
         70                  75                  80 caa aca gat gtt aag aca ttc ttg gaa gcc tta ccg cag gag tcc tgg      466
Gln Thr Asp Val Lys Thr Phe Leu Glu Ala Leu Pro Gln Glu Ser Trp
 85                  90                  95 caa aat aag cat gca ggt agt aat ggt aac aga gcc aca aat ggt gca      514
Gln Asn Lys His Ala Gly Ser Asn Gly Asn Arg Ala Thr Asn Gly Ala
100                 105                 110                 115 cca agc ctg gtc tcc agg ggg atg caa gga gca tct gct aac act cta      562
Pro Ser Leu Val Ser Arg Gly Met Gln Gly Ala Ser Ala Asn Thr Leu
                120                 125                 130
```

-continued

| | | |
|---|---|---|
| aac tct gaa acc agc aca aag agg gca gct gtg tac agg atg aat cgg<br>Asn Ser Glu Thr Ser Thr Lys Arg Ala Ala Val Tyr Arg Met Asn Arg<br>            135                  140                  145 | 610 |
| aac cac aga ggc ctc tgt gtc att gtc aac aac cac agc ttt acc tcc<br>Asn His Arg Gly Leu Cys Val Ile Val Asn Asn His Ser Phe Thr Ser<br>150                  155                  160 | 658 |
| ctg aag gac aga caa gga acc cat aaa gat gct gag atc ctg agt cat<br>Leu Lys Asp Arg Gln Gly Thr His Lys Asp Ala Glu Ile Leu Ser His<br>        165                  170                  175 | 706 |
| gtg ttc cag tgg ctt ggg ttc aca gtg cat ata cac aat aat gtg acg<br>Val Phe Gln Trp Leu Gly Phe Thr Val His Ile His Asn Asn Val Thr<br>180                  185                  190                  195 | 754 |
| aaa gtg gaa atg gag atg gtc ctg cag aag cag aag tgc aat cca gcc<br>Lys Val Glu Met Glu Met Val Leu Gln Lys Gln Lys Cys Asn Pro Ala<br>                200                  205                  210 | 802 |
| cat gcc gac ggg gac tgc ttc gtg ttc tgt att ctg acc cat ggg aga<br>His Ala Asp Gly Asp Cys Phe Val Phe Cys Ile Leu Thr His Gly Arg<br>        215                  220                  225 | 850 |
| ttt gga gct gtc tac tct tcg gat gag gcc ctc att ccc att cgg gag<br>Phe Gly Ala Val Tyr Ser Ser Asp Glu Ala Leu Ile Pro Ile Arg Glu<br>230                  235                  240 | 898 |
| atc atg tct cac ttc aca gcc ctg cag tgc cct aga ctg gct gaa aaa<br>Ile Met Ser His Phe Thr Ala Leu Gln Cys Pro Arg Leu Ala Glu Lys<br>        245                  250                  255 | 946 |
| cct aaa ctc ttt ttc atc cag gcc tgc caa ggt gaa gag ata cag cct<br>Pro Lys Leu Phe Phe Ile Gln Ala Cys Gln Gly Glu Glu Ile Gln Pro<br>260                  265                  270                  275 | 994 |
| tcc gta tcc atc gaa gca gat gct ctg aac cct gag cag gca ccc act<br>Ser Val Ser Ile Glu Ala Asp Ala Leu Asn Pro Glu Gln Ala Pro Thr<br>                280                  285                  290 | 1042 |
| tcc ctg cag gac agt att cct gcc gag gct gac ttc cta ctt ggt ctg<br>Ser Leu Gln Asp Ser Ile Pro Ala Glu Ala Asp Phe Leu Leu Gly Leu<br>        295                  300                  305 | 1090 |
| gcc act gtc cca ggc tat gta tcc ttt cgg cat gtg gag gaa ggc agc<br>Ala Thr Val Pro Gly Tyr Val Ser Phe Arg His Val Glu Glu Gly Ser<br>310                  315                  320 | 1138 |
| tgg tat att cag tct ctg tgt aat cat ctg aag aaa ttg gtc cca aga<br>Trp Tyr Ile Gln Ser Leu Cys Asn His Leu Lys Lys Leu Val Pro Arg<br>        325                  330                  335 | 1186 |
| cat gaa gac atc tta tcc atc ctc act gct gtc aac gat gat gtg agt<br>His Glu Asp Ile Leu Ser Ile Leu Thr Ala Val Asn Asp Asp Val Ser<br>340                  345                  350                  355 | 1234 |
| cga aga gtg gac aaa cag gga aca aag aaa cag atg ccc cag cct gct<br>Arg Arg Val Asp Lys Gln Gly Thr Lys Lys Gln Met Pro Gln Pro Ala<br>                360                  365                  370 | 1282 |
| ttc aca cta agg aaa aaa cta gta ttc cct gtg ccc ctg gat gca ctt<br>Phe Thr Leu Arg Lys Lys Leu Val Phe Pro Val Pro Leu Asp Ala Leu<br>        375                  380                  385 | 1330 |
| tca tta tagcagagag tttttgttgg ttcctagacc tcaaacgaat cattggctat<br>Ser Leu | 1386 |
| aacctccagc ctcctgccca gcacaggaat cggtggtctc cacctgtcat tctagaaaca | 1446 |
| ggaaacaccg tgttttctga cacagtcaat tctgattttc ttttcttttt gcaagtctaa | 1506 |
| atgttagaaa actttctttt ttttggagat agtctcattc tgtcacccag actgagtgc | 1566 |
| agggggcaa tcacggctca ctgtagtctc ggcctcccgg gctcgggctg tcctcccgcc | 1626 |
| tcagcttccc aagtagctgg gaccacaggt gtgtaccacc gtgcccggat ttttttattt | 1686 |
| cctatttttt tgtagagatg gagggatctc accttgttgc acaggtgggt ttcaaactcc | 1746 |

-continued

```
taggcccaag tgatcctccc acctctgtcc ccaaaatact gggattatag gcacgagcca      1806
ccacacctgg ccagaaaact ttcattattg aagacttgga ttgtagcctt ggttttggat      1866
gtctattctg aagacagagt aattggcttt ggtttgtgca ggtacttttt ctttgagaca      1926
gagtcactcc gtcacctggg ctggagtgca gtggtgggat cactgttcac tgcagccttg      1986
acctcccagg ttcaagcgat cctcccacct cagcctccca agtagctgag actacaggtg      2046
tgtgtccatg cacagctaac ttttatttt ttttgtggag atggggtttc actatgttgc       2106
ctaagctggt ctcaaactcc tgggctcaag cgatcctccc acctca                     2152
```

<210> SEQ ID NO 2
<211> LENGTH: 389
<212> TYPE: PRT
<213> ORGANISM: Homo sapiens

<400> SEQUENCE: 2

```
Met Ile Phe Leu Leu Lys Asp Ser Leu Pro Lys Thr Glu Met Thr Ser
  1               5                  10                  15

Leu Ser Phe Leu Ala Phe Leu Glu Lys Gln Gly Lys Ile Asp Glu Asp
             20                  25                  30

Asn Leu Thr Cys Leu Glu Asp Leu Cys Lys Thr Val Val Pro Lys Leu
         35                  40                  45

Leu Arg Asn Ile Glu Lys Tyr Lys Arg Glu Lys Ala Ile Gln Ile Val
     50                  55                  60

Thr Pro Pro Val Asp Lys Glu Ala Glu Ser Tyr Gln Gly Glu Glu Glu
 65                  70                  75                  80

Leu Val Ser Gln Thr Asp Val Lys Thr Phe Leu Glu Ala Leu Pro Gln
             85                  90                  95

Glu Ser Trp Gln Asn Lys His Ala Gly Ser Asn Gly Asn Arg Ala Thr
            100                 105                 110

Asn Gly Ala Pro Ser Leu Val Ser Arg Gly Met Gln Gly Ala Ser Ala
        115                 120                 125

Asn Thr Leu Asn Ser Glu Thr Ser Thr Lys Arg Ala Ala Val Tyr Arg
    130                 135                 140

Met Asn Arg Asn His Arg Gly Leu Cys Val Ile Val Asn Asn His Ser
145                 150                 155                 160

Phe Thr Ser Leu Lys Asp Arg Gln Gly Thr His Lys Asp Ala Glu Ile
                165                 170                 175

Leu Ser His Val Phe Gln Trp Leu Gly Phe Thr Val His Ile His Asn
            180                 185                 190

Asn Val Thr Lys Val Glu Met Glu Met Val Leu Gln Lys Gln Lys Cys
        195                 200                 205

Asn Pro Ala His Ala Asp Gly Asp Cys Phe Val Phe Cys Ile Leu Thr
    210                 215                 220

His Gly Arg Phe Gly Ala Val Tyr Ser Ser Asp Glu Ala Leu Ile Pro
225                 230                 235                 240

Ile Arg Glu Ile Met Ser His Phe Thr Ala Leu Gln Cys Pro Arg Leu
                245                 250                 255

Ala Glu Lys Pro Lys Leu Phe Phe Ile Gln Ala Cys Gln Gly Glu Glu
            260                 265                 270

Ile Gln Pro Ser Val Ser Ile Glu Ala Asp Ala Leu Asn Pro Glu Gln
        275                 280                 285

Ala Pro Thr Ser Leu Gln Asp Ser Ile Pro Ala Glu Ala Asp Phe Leu
    290                 295                 300
```

```
Leu Gly Leu Ala Thr Val Pro Gly Tyr Val Ser Phe Arg His Val Glu
305                 310                 315                 320

Glu Gly Ser Trp Tyr Ile Gln Ser Leu Cys Asn His Leu Lys Lys Leu
            325                 330                 335

Val Pro Arg His Glu Asp Ile Leu Ser Ile Leu Thr Ala Val Asn Asp
            340                 345                 350

Asp Val Ser Arg Arg Val Asp Lys Gln Gly Thr Lys Lys Gln Met Pro
            355                 360                 365

Gln Pro Ala Phe Thr Leu Arg Lys Lys Leu Val Phe Pro Val Pro Leu
    370                 375                 380

Asp Ala Leu Ser Leu
385

<210> SEQ ID NO 3
<211> LENGTH: 389
<212> TYPE: PRT
<213> ORGANISM: Homo sapiens

<400> SEQUENCE: 3

Met Ile Phe Leu Leu Lys Asp Ser Leu Pro Lys Thr Glu Met Thr Ser
 1               5                  10                  15

Leu Ser Phe Leu Ala Phe Leu Glu Lys Gln Gly Lys Ile Asp Glu Asp
                20                  25                  30

Asn Leu Thr Cys Leu Glu Asp Leu Cys Lys Thr Val Val Pro Lys Leu
            35                  40                  45

Leu Arg Asn Ile Glu Lys Tyr Lys Arg Glu Lys Ala Ile Gln Ile Val
    50                  55                  60

Thr Pro Pro Val Asp Lys Glu Ala Glu Ser Tyr Gln Gly Glu Glu Glu
 65                  70                  75                  80

Leu Val Ser Gln Thr Asp Val Lys Thr Phe Leu Glu Ala Leu Pro Gln
                85                  90                  95

Glu Ser Trp Gln Asn Lys His Ala Gly Ser Asn Gly Asn Arg Ala Thr
            100                 105                 110

Asn Gly Ala Pro Ser Leu Val Ser Arg Gly Met Gln Gly Ala Ser Ala
    115                 120                 125

Asn Thr Leu Asn Ser Glu Thr Ser Thr Lys Arg Ala Ala Val Tyr Arg
130                 135                 140

Met Asn Arg Asn His Arg Gly Leu Cys Val Ile Val Asn Asn His Ser
145                 150                 155                 160

Phe Tyr Ser Leu Lys Asp Arg Gln Gly Thr His Lys Asp Ala Glu Ile
                165                 170                 175

Leu Ser His Val Phe Gln Trp Leu Gly Phe Thr Val His Ile His Asn
            180                 185                 190

Asn Val Thr Lys Val Glu Met Glu Met Val Leu Gln Lys Gln Lys Cys
    195                 200                 205

Asn Pro Ala His Pro Thr Gly Asp Cys Phe Val Phe Cys Ile Leu Thr
210                 215                 220

His Gly Arg Phe Gly Ala Val Tyr Ser Ser Asp Glu Ala Leu Ile Pro
225                 230                 235                 240

Ile Arg Glu Ile Met Ser His Phe Thr Ala Leu Gln Cys Pro Arg Leu
                245                 250                 255

Ala Glu Lys Pro Lys Leu Phe Phe Ile Gln Ala Cys Gln Gly Glu Glu
            260                 265                 270

Ile Gln Pro Ser Val Ser Ile Glu Ala Asp Ala Leu Asn Pro Glu Gln
    275                 280                 285
```

-continued

```
Ala Pro Thr Ser Leu Gln Asp Ser Ile Pro Ala Glu Ala Asp Phe Leu
    290                 295                 300

Leu Gly Leu Ala Thr Val Pro Gly Tyr Val Ser Phe Arg His Val Glu
305                 310                 315                 320

Glu Gly Ser Trp Tyr Ile Gln Ser Leu Cys Asn His Leu Lys Lys Leu
                325                 330                 335

Val Pro Arg His Glu Asp Ile Leu Ser Ile Leu Thr Ala Val Asn Asp
                340                 345                 350

Asp Val Ser Arg Arg Val Asp Lys Gln Gly Thr Lys Lys Gln Met Pro
            355                 360                 365

Gln Pro Ala Phe Thr Leu Arg Lys Lys Leu Val Phe Pro Val Pro Leu
    370                 375                 380

Asp Ala Leu Ser Leu
385

<210> SEQ ID NO 4
<211> LENGTH: 303
<212> TYPE: PRT
<213> ORGANISM: Homo sapiens

<400> SEQUENCE: 4

Met Ala Asp Asp Gln Gly Cys Ile Glu Glu Gln Gly Val Glu Asp Ser
  1               5                  10                  15

Ala Asn Glu Asp Ser Val Asp Ala Lys Pro Asp Arg Ser Ser Phe Val
             20                  25                  30

Pro Ser Leu Phe Ser Lys Lys Lys Asn Val Thr Met Arg Ser Ile
         35                  40                  45

Lys Thr Thr Arg Asp Arg Val Pro Thr Tyr Gln Tyr Asn Met Asn Phe
 50                  55                  60

Glu Lys Leu Gly Lys Cys Ile Ile Asn Asn Lys Asn Phe Asp Lys
 65                  70                  75                  80

Val Thr Gly Met Gly Val Arg Asn Gly Thr Asp Lys Asp Ala Glu Ala
                 85                  90                  95

Leu Phe Lys Cys Phe Arg Ser Leu Gly Phe Asp Val Ile Val Tyr Asn
             100                 105                 110

Asp Cys Ser Cys Ala Lys Met Gln Asp Leu Leu Lys Lys Ala Ser Glu
         115                 120                 125

Glu Asp His Thr Asn Ala Ala Cys Phe Ala Cys Ile Leu Leu Ser His
     130                 135                 140

Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Cys Arg Gly Thr Glu Leu Asp
            180                 185                 190

Asp Gly Ile Gln Ala Asp Ser Gly Pro Ile Asn Asp Thr Asp Ala Asn
        195                 200                 205

Pro Arg Tyr Lys Ile Pro Val Glu Ala Asp Phe Leu Phe Ala Tyr Ser
    210                 215                 220

Thr Val Pro Gly Tyr Tyr Ser Trp Arg Ser Pro Gly Arg Gly Ser Trp
225                 230                 235                 240

Phe Val Gln Ala Leu Cys Ser Ile Leu Glu Glu His Gly Lys Asp Leu
                245                 250                 255

Glu Ile Met Gln Ile Leu Thr Arg Val Asn Asp Arg Val Ala Arg His
```

```
                    260                 265                 270
Phe Glu Ser Gln Ser Asp Asp Pro His Phe His Glu Lys Lys Gln Ile
                275                 280                 285
Pro Cys Val Val Ser Met Leu Thr Lys Glu Leu Tyr Phe Ser Gln
                290                 295                 300

<210> SEQ ID NO 5
<211> LENGTH: 277
<212> TYPE: PRT
<213> ORGANISM: Homo sapiens

<400> SEQUENCE: 5

Met Glu Asn Thr Glu Asn Ser Val Asp Ser Lys Ser Ile Lys Asn Leu
  1               5                  10                  15
Glu Pro Lys Ile Ile His Gly Ser Glu Ser Met Asp Ser Gly Ile Ser
                 20                  25                  30
Leu Asp Asn Ser Tyr Lys Met Asp Tyr Pro Glu Met Gly Leu Cys Ile
             35                  40                  45
Ile Ile Asn Asn Lys Asn Phe His Lys Ser Thr Gly Met Thr Ser Arg
         50                  55                  60
Ser Gly Thr Asp Val Asp Ala Ala Asn Leu Arg Glu Thr Phe Arg Asn
 65                  70                  75                  80
Leu Lys Tyr Glu Val Arg Asn Lys Asn Asp Leu Thr Arg Glu Glu Ile
                 85                  90                  95
Val Glu Leu Met Arg Asp Val Ser Lys Glu Asp His Ser Lys Arg Ser
                100                 105                 110
Ser Phe Val Cys Val Leu Leu Ser His Gly Glu Glu Gly Ile Ile Phe
            115                 120                 125
Gly Thr Asn Gly Pro Val Asp Leu Lys Lys Ile Thr Asn Phe Phe Arg
        130                 135                 140
Gly Asp Arg Cys Arg Ser Leu Thr Gly Lys Pro Lys Leu Phe Ile Ile
145                 150                 155                 160
Gln Ala Cys Arg Gly Thr Glu Leu Asp Cys Gly Ile Glu Thr Asp Ser
                165                 170                 175
Gly Val Asp Asp Asp Met Ala Cys His Lys Ile Pro Val Asp Ala Asp
            180                 185                 190
Phe Leu Tyr Ala Tyr Ser Thr Ala Pro Gly Tyr Tyr Ser Trp Arg Asn
        195                 200                 205
Ser Lys Asp Gly Ser Trp Phe Ile Gln Ser Leu Cys Ala Met Leu Lys
    210                 215                 220
Gln Tyr Ala Asp Lys Leu Glu Phe Met His Ile Leu Thr Arg Val Asn
225                 230                 235                 240
Arg Lys Val Ala Thr Glu Phe Glu Ser Phe Ser Phe Asp Ala Thr Phe
                245                 250                 255
His Ala Lys Lys Gln Ile Pro Cys Ile Val Ser Met Leu Thr Lys Glu
            260                 265                 270
Leu Tyr Phe Tyr His
        275

<210> SEQ ID NO 6
<211> LENGTH: 293
<212> TYPE: PRT
<213> ORGANISM: Homo sapiens

<400> SEQUENCE: 6

Met Ser Ser Ala Ser Gly Leu Arg Arg Gly His Pro Ala Gly Gly Glu
```

```
  1               5                   10                  15
Glu Asn Met Thr Glu Thr Asp Ala Phe Tyr Lys Arg Glu Met Phe Asp
                20                  25                  30

Pro Ala Glu Lys Tyr Lys Met Asp His Arg Arg Gly Ile Ala Leu
            35                  40                  45

Ile Phe Asn His Glu Arg Phe Phe Trp His Leu Thr Leu Pro Glu Arg
        50                  55                  60

Arg Arg Thr Cys Ala Asp Arg Asp Asn Leu Thr Arg Arg Phe Ser Asp
65                      70                  75                  80

Leu Gly Phe Glu Val Lys Cys Phe Asn Asp Leu Lys Ala Glu Glu Leu
                85                  90                  95

Leu Leu Lys Ile His Glu Val Ser Thr Val Ser His Ala Asp Ala Asp
            100                 105                 110

Cys Phe Val Cys Val Phe Leu Ser His Gly Glu Gly Asn His Ile Tyr
        115                 120                 125

Ala Tyr Asp Ala Lys Ile Glu Ile Gln Thr Leu Thr Gly Leu Phe Lys
        130                 135                 140

Gly Asp Lys Cys His Ser Leu Val Gly Lys Pro Lys Ile Phe Ile Ile
145                 150                 155                 160

Gln Ala Cys Arg Gly Asn Gln His Asp Val Pro Val Ile Pro Leu Asp
                165                 170                 175

Val Val Asp Asn Gln Thr Glu Lys Leu Asp Thr Asn Ile Thr Glu Val
            180                 185                 190

Asp Ala Ala Ser Val Tyr Thr Leu Pro Ala Gly Ala Asp Phe Leu Met
        195                 200                 205

Cys Tyr Ser Val Ala Glu Gly Tyr Tyr Ser His Arg Glu Thr Val Asn
    210                 215                 220

Gly Ser Trp Tyr Ile Gln Asp Leu Cys Glu Met Leu Gly Lys Tyr Gly
225                 230                 235                 240

Ser Ser Leu Glu Phe Thr Glu Leu Leu Thr Leu Val Asn Arg Lys Val
                245                 250                 255

Ser Gln Arg Arg Val Asp Phe Cys Lys Asp Pro Ser Ala Ile Gly Lys
            260                 265                 270

Lys Gln Val Pro Cys Phe Ala Ser Met Leu Thr Lys Lys Leu His Phe
        275                 280                 285

Phe Pro Lys Ser Asn
    290

<210> SEQ ID NO 7
<211> LENGTH: 404
<212> TYPE: PRT
<213> ORGANISM: Homo sapiens

<400> SEQUENCE: 7

Met Ala Asp Lys Val Leu Lys Glu Lys Arg Lys Leu Phe Ile Arg Ser
  1               5                   10                  15

Met Gly Glu Gly Thr Ile Asn Gly Leu Leu Asp Glu Leu Leu Gln Thr
                20                  25                  30

Arg Val Leu Asn Lys Glu Glu Met Glu Lys Val Lys Arg Glu Asn Ala
            35                  40                  45

Thr Val Met Asp Lys Thr Arg Ala Leu Ile Asp Ser Val Ile Pro Lys
        50                  55                  60

Gly Ala Gln Ala Cys Gln Ile Cys Ile Thr Tyr Ile Cys Glu Glu Asp
65                  70                  75                  80
```

```
Ser Tyr Leu Ala Gly Thr Leu Gly Leu Ser Ala Asp Gln Thr Ser Gly
                85                  90                  95

Asn Tyr Leu Asn Met Gln Asp Ser Gln Gly Val Leu Ser Ser Phe Pro
               100                 105                 110

Ala Pro Gln Ala Val Gln Asp Asn Pro Ala Met Pro Thr Ser Ser Gly
               115                 120                 125

Ser Glu Gly Asn Val Lys Leu Cys Ser Leu Glu Ala Gln Arg Ile
    130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
               165                 170                 175

Pro Arg Arg Thr Gly Ala Glu Val Asp Ile Thr Gly Met Thr Met Leu
               180                 185                 190

Leu Gln Asn Leu Gly Tyr Ser Val Asp Val Lys Lys Asn Leu Thr Ala
               195                 200                 205

Ser Asp Met Thr Thr Glu Leu Glu Ala Phe Ala His Arg Pro Glu His
    210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
               245                 250                 255

Gln Leu Asn Ala Ile Phe Asn Met Leu Asn Thr Lys Asn Cys Pro Ser
               260                 265                 270

Leu Lys Asp Lys Pro Lys Val Ile Ile Gln Ala Cys Arg Gly Asp
               275                 280                 285

Ser Pro Gly Val Val Trp Phe Lys Asp Ser Val Gly Val Ser Gly Asn
    290                 295                 300

Leu Ser Leu Pro Thr Thr Glu Glu Phe Glu Asp Asp Ala Ile Lys Lys
305                 310                 315                 320

Ala His Ile Glu Lys Asp Phe Ile Ala Phe Cys Ser Ser Thr Pro Asp
               325                 330                 335

Asn Val Ser Trp Arg His Pro Thr Met Gly Ser Val Phe Ile Gly Arg
               340                 345                 350

Leu Ile Glu His Met Gln Glu Tyr Ala Cys Ser Cys Asp Val Glu Glu
               355                 360                 365

Ile Phe Arg Lys Val Arg Phe Ser Phe Glu Gln Pro Asp Gly Arg Ala
    370                 375                 380

Gln Met Pro Thr Thr Glu Arg Val Thr Leu Thr Arg Cys Phe Tyr Leu
385                 390                 395                 400

Phe Pro Gly His

<210> SEQ ID NO 8
<211> LENGTH: 377
<212> TYPE: PRT
<213> ORGANISM: Homo sapiens

<400> SEQUENCE: 8

Met Ala Glu Gly Asn His Arg Lys Lys Pro Leu Lys Val Leu Glu Ser
  1               5                  10                  15

Leu Gly Lys Asp Phe Leu Thr Gly Val Leu Asp Asn Leu Val Glu Gln
                 20                  25                  30

Asn Val Leu Asn Trp Lys Glu Glu Lys Lys Lys Tyr Tyr Asp Ala
             35                  40                  45
```

```
Lys Thr Glu Asp Lys Val Arg Val Met Ala Asp Ser Met Gln Glu Lys
     50                  55                  60

Gln Arg Met Ala Gly Gln Met Leu Leu Gln Thr Phe Asn Ile Asp
 65                  70                  75                  80

Gln Ile Ser Pro Asn Lys Lys Ala His Pro Asn Met Glu Ala Gly Pro
                 85                  90                  95

Pro Glu Ser Gly Glu Ser Thr Asp Ala Leu Lys Leu Cys Pro His Glu
                100                 105                 110

Glu Phe Leu Arg Leu Cys Lys Glu Arg Ala Glu Glu Ile Tyr Pro Ile
             115                 120                 125

Lys Glu Arg Asn Asn Arg Thr Arg Leu Ala Leu Ile Ile Cys Asn Thr
        130                 135                 140

Glu Phe Asp His Leu Pro Pro Arg Asn Gly Ala Asp Phe Asp Ile Thr
145                 150                 155                 160

Gly Met Lys Glu Leu Leu Glu Gly Leu Asp Tyr Ser Val Asp Val Glu
                165                 170                 175

Glu Asn Leu Thr Ala Arg Asp Met Glu Ser Ala Leu Arg Ala Phe Ala
            180                 185                 190

Thr Arg Pro Glu His Lys Ser Ser Asp Ser Thr Phe Leu Val Leu Met
        195                 200                 205

Ser His Gly Ile Leu Glu Gly Ile Cys Gly Thr Val His Asp Glu Lys
    210                 215                 220

Lys Pro Asp Val Leu Leu Tyr Asp Thr Ile Phe Gln Ile Phe Asn Asn
225                 230                 235                 240

Arg Asn Cys Leu Ser Leu Lys Asp Lys Pro Lys Val Ile Ile Val Gln
                245                 250                 255

Ala Cys Arg Gly Ala Asn Arg Gly Glu Leu Trp Val Arg Asp Ser Pro
            260                 265                 270

Ala Ser Leu Glu Val Ala Ser Ser Gln Ser Ser Glu Asn Leu Glu Glu
        275                 280                 285

Asp Ala Val Tyr Lys Thr His Val Glu Lys Asp Phe Ile Ala Phe Cys
    290                 295                 300

Ser Ser Thr Pro His Asn Val Ser Trp Arg Asp Ser Thr Met Gly Ser
305                 310                 315                 320

Ile Phe Ile Thr Gln Leu Ile Thr Cys Phe Gln Lys Tyr Ser Trp Cys
                325                 330                 335

Cys His Leu Glu Glu Val Phe Arg Lys Val Gln Gln Ser Phe Glu Thr
            340                 345                 350

Pro Arg Ala Lys Ala Gln Met Pro Thr Ile Glu Arg Leu Ser Met Thr
        355                 360                 365

Arg Tyr Phe Tyr Leu Phe Pro Gly Asn
    370                 375

<210> SEQ ID NO 9
<211> LENGTH: 435
<212> TYPE: PRT
<213> ORGANISM: Homo sapiens

<400> SEQUENCE: 9

Met Ala Ala Asp Arg Gly Arg Arg Ile Leu Gly Val Cys Gly Met His
 1               5                  10                  15

Pro His His Gln Glu Thr Leu Lys Lys Asn Arg Val Val Leu Ala Lys
                 20                  25                  30

Gln Leu Leu Leu Ser Glu Leu Leu Glu His Leu Leu Glu Lys Asp Ile
             35                  40                  45
```

```
Ile Thr Leu Glu Met Arg Glu Leu Ile Gln Ala Lys Val Gly Ser Phe
 50                  55                  60

Ser Gln Asn Val Glu Leu Leu Asn Leu Leu Pro Lys Arg Gly Pro Gln
 65                  70                  75                  80

Ala Phe Asp Ala Phe Cys Glu Ala Leu Arg Glu Thr Lys Gln Gly His
                 85                  90                  95

Leu Glu Asp Met Leu Leu Thr Thr Leu Ser Gly Leu Gln His Val Leu
            100                 105                 110

Pro Pro Leu Ser Cys Asp Tyr Asp Leu Ser Leu Pro Phe Pro Val Cys
            115                 120                 125

Glu Ser Cys Pro Leu Tyr Lys Lys Leu Arg Leu Ser Thr Asp Thr Val
130                 135                 140

Glu His Ser Leu Asp Asn Lys Asp Gly Pro Val Cys Leu Gln Val Lys
145                 150                 155                 160

Pro Cys Thr Pro Glu Phe Tyr Gln Thr His Phe Gln Leu Ala Tyr Arg
                165                 170                 175

Leu Gln Ser Arg Pro Arg Gly Leu Ala Leu Val Leu Ser Asn Val His
            180                 185                 190

Phe Thr Gly Glu Lys Glu Leu Glu Phe Arg Ser Gly Gly Asp Val Asp
            195                 200                 205

His Ser Thr Leu Val Thr Leu Phe Lys Leu Leu Gly Tyr Asp Val His
            210                 215                 220

Val Leu Cys Asp Gln Thr Ala Gln Glu Met Gln Glu Lys Leu Gln Asn
225                 230                 235                 240

Phe Ala Gln Leu Pro Ala His Arg Val Thr Asp Ser Cys Ile Val Ala
                245                 250                 255

Leu Leu Ser His Gly Val Glu Gly Ala Ile Tyr Gly Val Asp Gly Lys
            260                 265                 270

Leu Leu Gln Leu Gln Glu Val Phe Gln Leu Phe Asp Asn Ala Asn Cys
            275                 280                 285

Pro Ser Leu Gln Asn Lys Pro Lys Met Phe Phe Ile Gln Ala Cys Arg
            290                 295                 300

Gly Asp Glu Thr Asp Arg Gly Val Asp Gln Gln Asp Gly Lys Asn His
305                 310                 315                 320

Ala Gly Ser Pro Gly Cys Glu Ser Asp Ala Gly Lys Glu Lys Leu
                325                 330                 335

Pro Lys Met Arg Leu Pro Thr Arg Ser Asp Met Ile Cys Gly Tyr Ala
            340                 345                 350

Cys Leu Lys Gly Thr Ala Ala Met Arg Asn Thr Lys Arg Gly Ser Trp
            355                 360                 365

Tyr Ile Glu Ala Leu Ala Gln Val Phe Ser Glu Arg Ala Cys Asp Met
            370                 375                 380

His Val Ala Asp Met Leu Val Lys Val Asn Ala Leu Ile Lys Asp Arg
385                 390                 395                 400

Glu Gly Tyr Ala Pro Gly Thr Glu Phe His Arg Cys Lys Glu Met Ser
                405                 410                 415

Glu Tyr Cys Ser Thr Leu Cys Arg His Leu Tyr Leu Phe Pro Gly His
            420                 425                 430

Pro Pro Thr
        435

<210> SEQ ID NO 10
<211> LENGTH: 503
```

<212> TYPE: PRT
<213> ORGANISM: Caenorhabditis elegans

<400> SEQUENCE: 10

```
Met Met Arg Gln Asp Arg Arg Ser Leu Leu Glu Arg Asn Ile Met Met
 1               5                  10                  15

Phe Ser Ser His Leu Lys Val Asp Glu Ile Leu Glu Val Leu Ile Ala
             20                  25                  30

Lys Gln Val Leu Asn Ser Asp Asn Gly Asp Met Ile Asn Ser Cys Gly
         35                  40                  45

Thr Val Arg Glu Lys Arg Arg Glu Ile Val Lys Ala Val Gln Arg Arg
     50                  55                  60

Gly Asp Val Ala Phe Asp Ala Phe Tyr Asp Ala Leu Arg Ser Thr Gly
 65                  70                  75                  80

His Glu Gly Leu Ala Glu Val Leu Glu Pro Leu Ala Arg Ser Val Asp
                 85                  90                  95

Ser Asn Ala Val Glu Phe Glu Cys Pro Met Ser Pro Ala Ser His Arg
            100                 105                 110

Arg Ser Arg Ala Leu Ser Pro Ala Gly Tyr Thr Ser Pro Thr Arg Val
        115                 120                 125

His Arg Asp Ser Val Ser Val Ser Ser Phe Thr Ser Tyr Gln Asp
    130                 135                 140

Ile Tyr Ser Arg Ala Arg Ser Arg Ser Arg Ala Leu His Ser
145                 150                 155                 160

Ser Asp Arg His Asn Tyr Ser Pro Pro Val Asn Ala Phe Pro Ser
                165                 170                 175

Gln Pro Ser Ser Ala Asn Ser Ser Phe Thr Gly Cys Ser Ser Leu Gly
            180                 185                 190

Tyr Ser Ser Arg Asn Arg Ser Phe Ser Lys Ala Ser Gly Pro Thr
        195                 200                 205

Gln Tyr Ile Phe His Glu Glu Asp Met Asn Phe Val Asp Ala Pro Thr
    210                 215                 220

Ile Ser Arg Val Phe Asp Glu Lys Thr Met Tyr Arg Asn Phe Ser Ser
225                 230                 235                 240

Pro Arg Gly Met Cys Leu Ile Ile Asn Asn Glu His Phe Glu Gln Met
                245                 250                 255

Pro Thr Arg Asn Gly Thr Lys Ala Asp Lys Asp Asn Leu Thr Asn Leu
            260                 265                 270

Phe Arg Cys Met Gly Tyr Thr Val Ile Cys Lys Asp Asn Leu Thr Gly
        275                 280                 285

Arg Gly Met Leu Leu Thr Ile Arg Asp Phe Ala Lys His Glu Ser His
    290                 295                 300

Gly Asp Ser Ala Ile Leu Val Ile Leu Ser His Gly Glu Glu Asn Val
305                 310                 315                 320

Ile Ile Gly Val Asp Asp Ile Pro Ile Ser Thr His Glu Ile Tyr Asp
                325                 330                 335

Leu Leu Asn Ala Ala Asn Ala Pro Arg Leu Ala Asn Lys Pro Lys Ile
            340                 345                 350

Val Phe Val Gln Ala Cys Arg Gly Glu Arg Arg Asp Asn Gly Phe Pro
        355                 360                 365

Val Leu Asp Ser Val Asp Gly Val Pro Ala Phe Leu Arg Arg Gly Trp
    370                 375                 380

Asp Asn Arg Asp Gly Pro Leu Phe Asn Phe Leu Gly Cys Val Arg Pro
385                 390                 395                 400
```

```
Gln Val Gln Gln Val Trp Arg Lys Lys Pro Ser Gln Ala Asp Ile Leu
                405                 410                 415

Ile Arg Tyr Ala Thr Thr Ala Gln Tyr Val Ser Trp Arg Asn Ser Ala
            420                 425                 430

Arg Gly Ser Trp Phe Ile Gln Ala Val Cys Glu Val Phe Ser Thr His
        435                 440                 445

Ala Lys Asp Met Asp Val Val Glu Leu Leu Thr Glu Val Asn Lys Lys
    450                 455                 460

Val Ala Cys Gly Phe Gln Thr Ser Gln Gly Ser Asn Ile Leu Lys Gln
465                 470                 475                 480

Met Pro Glu Met Thr Ser Arg Leu Leu Lys Lys Phe Tyr Phe Trp Pro
                485                 490                 495

Glu Ala Arg Asn Ser Ala Val
            500

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 11
ccatcgaagc agatgaaccc tgag                                            24

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 12
aggttggctg aagatctgtt taagcacccc                                      30

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 13 cctttttgagc aagttcagcc tggttaagtc c                                    31

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 14
cagaggtggc ttatgagtat tccttccagg g                                     31

<210> SEQ ID NO 15
<211> LENGTH: 5
<212> TYPE: PRT
<213> ORGANISM: Homo sapiens

<400> SEQUENCE: 15

Gln Ala Cys Arg Gly
```

```
1               5

<210> SEQ ID NO 16
<211> LENGTH: 5
<212> TYPE: PRT
<213> ORGANISM: Homo sapiens

<400> SEQUENCE: 16

Gln Ala Cys Gln Gly
 1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: synthetic
      tetrapeptide

<400> SEQUENCE: 17

Asp Glu Val Asp
 1
```